US008475803B2

(12) United States Patent
Olwill et al.

(10) Patent No.: US 8,475,803 B2
(45) Date of Patent: Jul. 2, 2013

(54) ASSAYS FOR DIAGNOSIS OF TUBERCULOSIS AND USES THEREOF

(75) Inventors: Shane A. Olwill, Belfast (GB); Richard J. Buick, Belfast (GB); Hangfai Kwok, Belfast (GB); James A. Johnston, Belfast (GB)

(73) Assignee: Fusion Antibodies Limited, Belfast (GB)

( * ) Notice: Subject to any disclaimer, the term of this patent is extended or adjusted under 35 U.S.C. 154(b) by 199 days.

(21) Appl. No.: 11/919,530

(22) PCT Filed: May 2, 2006

(86) PCT No.: PCT/GB2006/001589
§ 371 (c)(1),
(2), (4) Date: Dec. 20, 2007

(87) PCT Pub. No.: WO2006/117538
PCT Pub. Date: Nov. 9, 2006

(65) Prior Publication Data
US 2009/0053258 A1    Feb. 26, 2009

(30) Foreign Application Priority Data

Apr. 29, 2005 (GB) ................... 0508701.0
Oct. 25, 2005 (GB) ................... 0521718.7
Jan. 18, 2006 (GB) ................... 0600991.4

(51) Int. Cl.
*A61K 39/00* (2006.01)
*C12Q 1/02* (2006.01)

(52) U.S. Cl.
USPC ........ 424/190.1; 435/6.15; 435/7.32; 435/29; 422/430

(58) Field of Classification Search
None
See application file for complete search history.

(56) References Cited

U.S. PATENT DOCUMENTS

| | | | | |
|---|---|---|---|---|
| 4,444,879 A | * | 4/1984 | Foster et al. | 435/7.95 |
| 6,048,543 A | * | 4/2000 | Schneider et al. | 424/442 |
| 6,291,190 B1 | * | 9/2001 | Behr et al. | 435/7.1 |
| 7,083,796 B2 | * | 8/2006 | Skeiky et al. | 424/248.1 |
| 7,135,280 B2 | * | 11/2006 | Lalvani | 435/4 |
| 7,311,922 B1 | * | 12/2007 | Skeiky et al. | 424/248.1 |
| 7,363,166 B2 | * | 4/2008 | Brahmachari et al. | 702/19 |
| 7,393,540 B2 | * | 7/2008 | James et al. | 424/248.1 |
| 7,572,597 B2 | * | 8/2009 | Lalvani et al. | 435/7.32 |

(Continued)

FOREIGN PATENT DOCUMENTS

| | | |
|---|---|---|
| WO | WO 98/53075 | 11/1998 |
| WO | WO 98/53076 | 11/1998 |

(Continued)

OTHER PUBLICATIONS

Cumus, JC et al, Microbiology, 2002, vol. 148, pp. 2967-2973, Re-annotation of the genome sequence of *Mycobacterium tuberculosis* H37Rv.*

(Continued)

*Primary Examiner* — Albert Navarro
*Assistant Examiner* — Ginny Portner
(74) *Attorney, Agent, or Firm* — Drinker Biddle & Reath LLP

(57) ABSTRACT

The invention relates to the identification of mycobacterial antigens which are highly immunogenic and which may be used in assays and methods for the diagnosis of tuberculosis and the discrimination between infected animals and animals previously exposed to vaccines.

20 Claims, 15 Drawing Sheets

Diagram 1

Outline of the strain specificity of mycobacterial protein / fragments suitable for diagnostic or immune stimulation purposes.

U.S. PATENT DOCUMENTS

| | | | |
|---|---|---|---|
| 2003/0039963 A1* | 2/2003 | Brahmachari et al. | 435/6 |
| 2003/0129601 A1* | 7/2003 | Cole | 435/6 |
| 2003/0175294 A1* | 9/2003 | Skeiky et al. | 424/190.1 |
| 2004/0086523 A1* | 5/2004 | Skeiky et al. | 424/190.1 |
| 2004/0121322 A9* | 6/2004 | Cole | 435/6 |
| 2004/0197896 A1* | 10/2004 | Cole | 435/252.3 |
| 2004/0241826 A1* | 12/2004 | James et al. | 435/252.3 |
| 2005/0220811 A1* | 10/2005 | Cole et al. | 424/200.1 |

FOREIGN PATENT DOCUMENTS

| | | | |
|---|---|---|---|
| WO | 0011214 | * | 3/2000 |
| WO | 01/98460 | * | 12/2001 |
| WO | WO 01/98460 | | 12/2001 |
| WO | 02/072792 | * | 9/2002 |
| WO | 03/004520 | * | 1/2003 |

OTHER PUBLICATIONS

Karakousis et al, Sep. 7, 2004, vol. 200(5) Journal of Experimental Medicine, 647-657 and appendix pp. 1-85, Dormancy Phenotype Displayed by Extracellular *Mycobacterium tuberculosis* withing ARtificial Granulomas in Mice.*

Cole, St et al, Nature, vol. 396, Nov. 12, 1998, pp. 190-198 and Nature Jun. 11, 1998, vol. 393, pp. 537-544, plus appendix Table 1. (total of 27 pages).*

* cited by examiner

Figure 1. Outline of the strain specificity of mycobacterial protein / fragments suitable for diagnostic or immune stimulation purposes.

PCR of rv2224c fragment from genomic DNA:

Analysis of protein purity and quantity by total protein staining with Coomassie Blue

Figure 5. Coomassie Blue stain of purified mycobacterial recombinant proteins

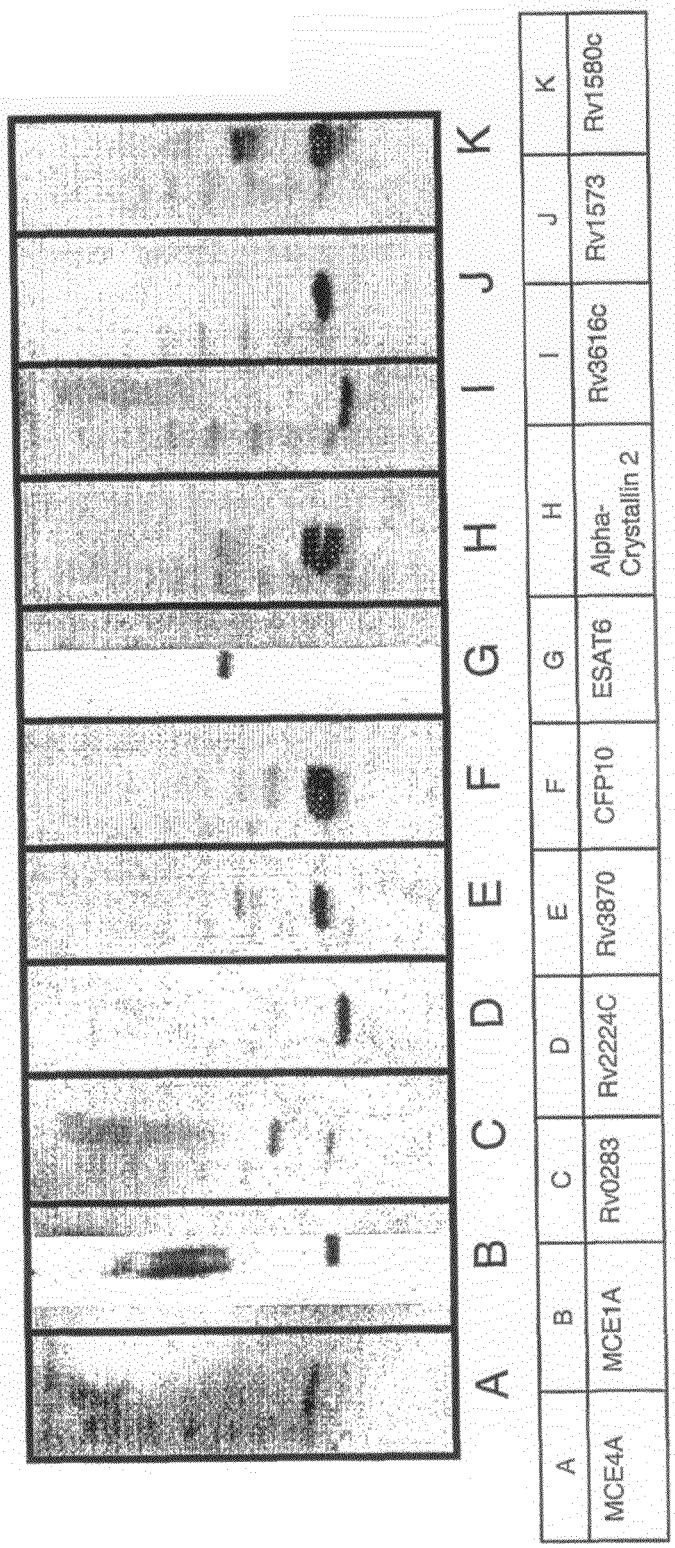
Figure 6. Western blots showing specific detection of mycobacterial proteins by rabbit polyclonal antibodies. Rabbit models were immunised with purified mycobacterial recombinant protein. In each case the rabbit host produced a strong specific immune response.

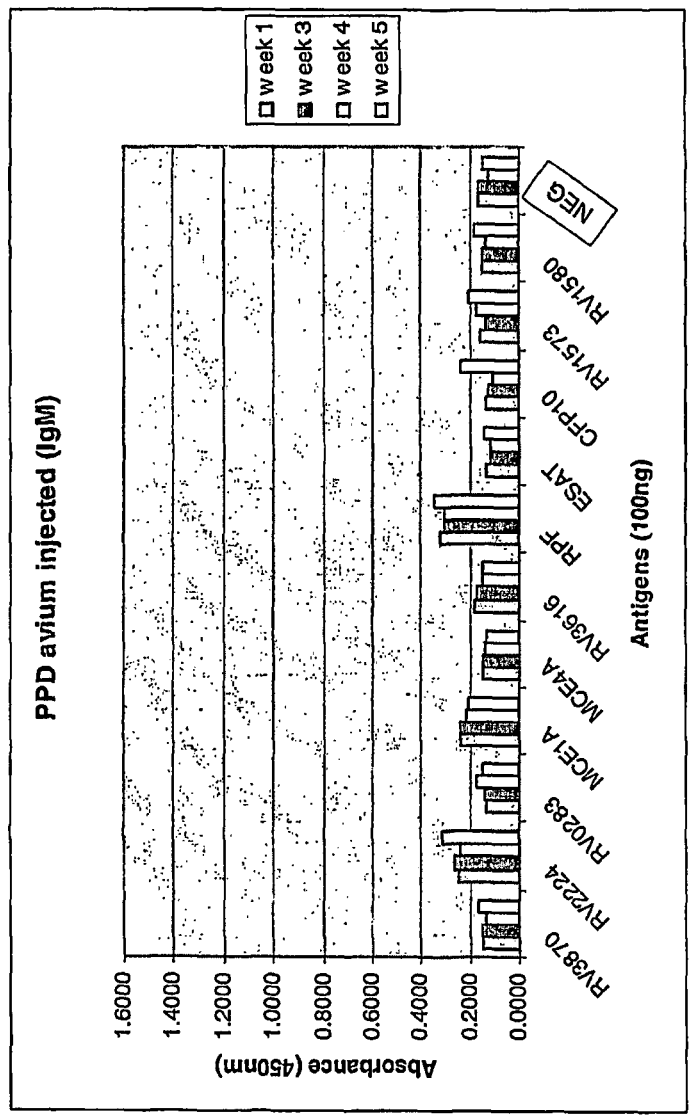
Figure 7. ELISA screen of *M. bovis* target proteins using rabbit serum from animals immunised with avian PPD. Serum was tested for presence of target specific IgM.

Figure 8. ELISA screen of *M. bovis* target proteins using rabbit serum from animals immunised with avian PPD. Serum was tested for presence of target specific IgG.

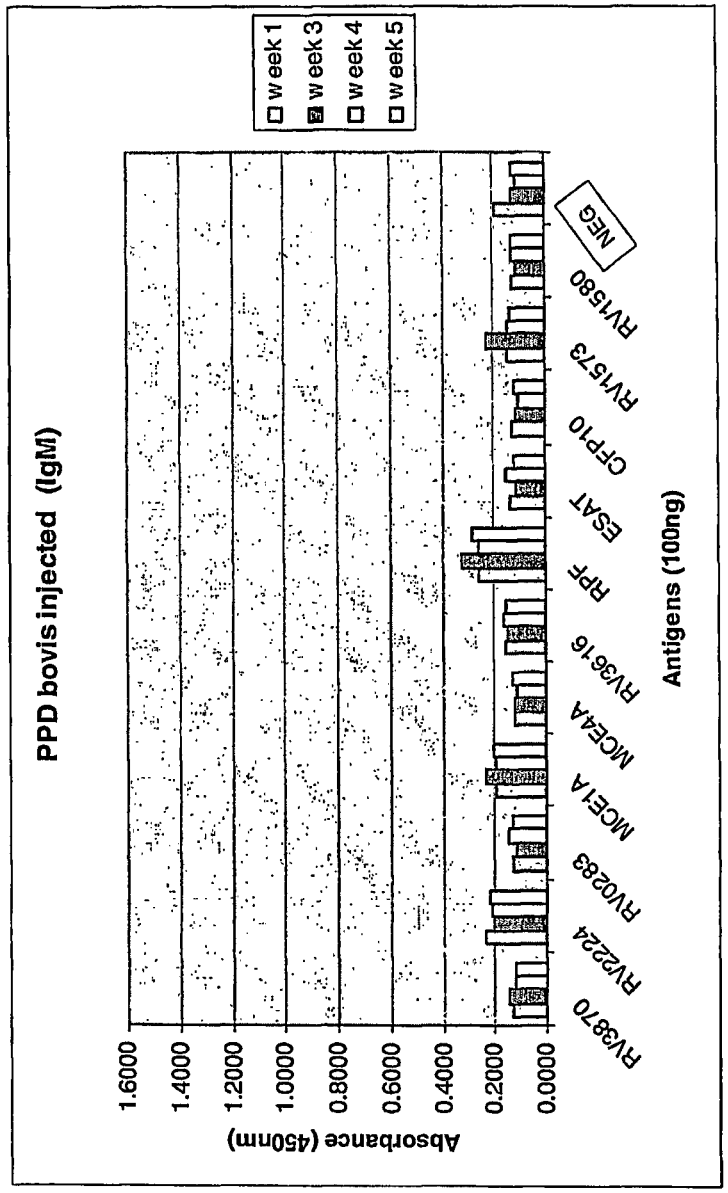
Figure 9. ELISA screen of *M. bovis* target proteins using rabbit serum from animals immunised with bovine PPD. Serum was t

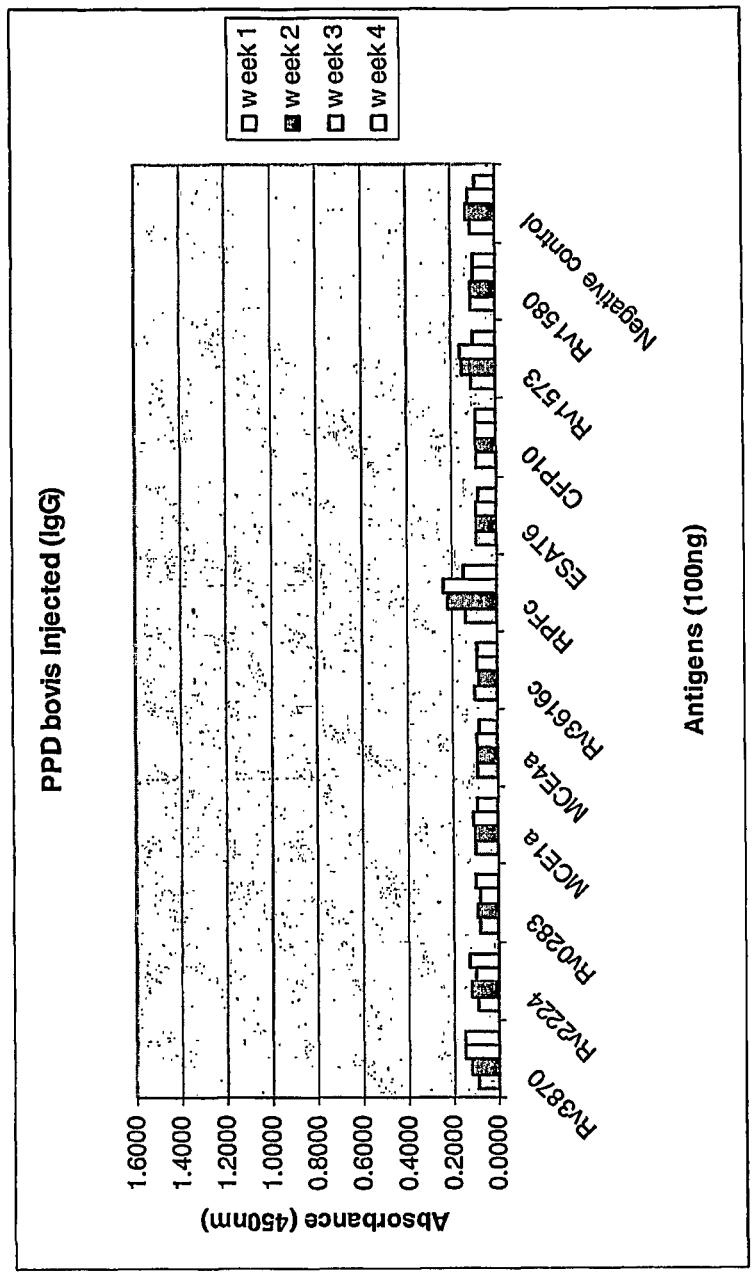
Figure 10. ELISA screen of *M. bovis* target proteins using rabbit serum from animals immunised with avian PPD. Serum was tested for presence of target specific IgG.

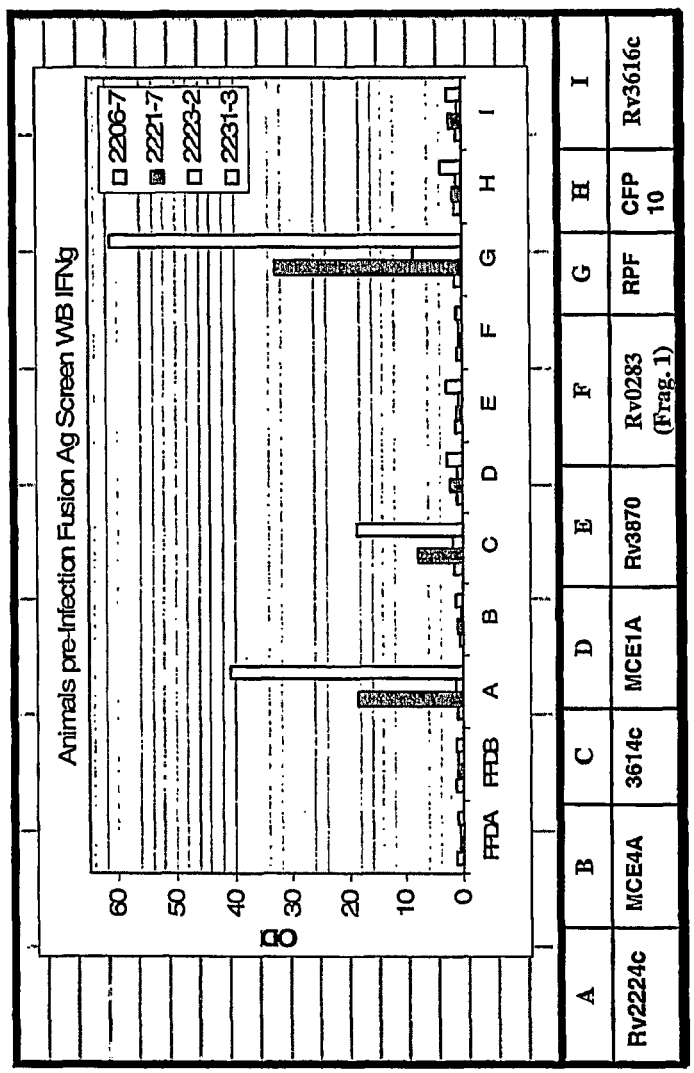
| A | B | C | D | E | F | G | H | I |
|---|---|---|---|---|---|---|---|---|
| Rv2224c | MCE4A | 3614c | MCE1A | Rv3870 | Rv0283 (Frag. 1) | RPF | CFP 10 | Rv3616c |
Figure 11. Cell Mediated Immunity Assay displaying results obtained when M. bovis proteins / fragments were tested against TB negative pre-infection bovine samples.

Figure 12. Cell Mediated Immunity Assay indicating the ability of M. bovis proteins to detect infection in bovine samples.

Figure 13. A western blot showing detection of early M. *bovis* TB Infection in bovine samples (Sample tested positive for antibody to response to Alpha crystalin 2, Rv1573 and Rv1580c).

Figure 14. A western blot showing detection of late M. *bovis* TB Infection in bovine samples (Sample tested positive for antibody to response to Rv1573).

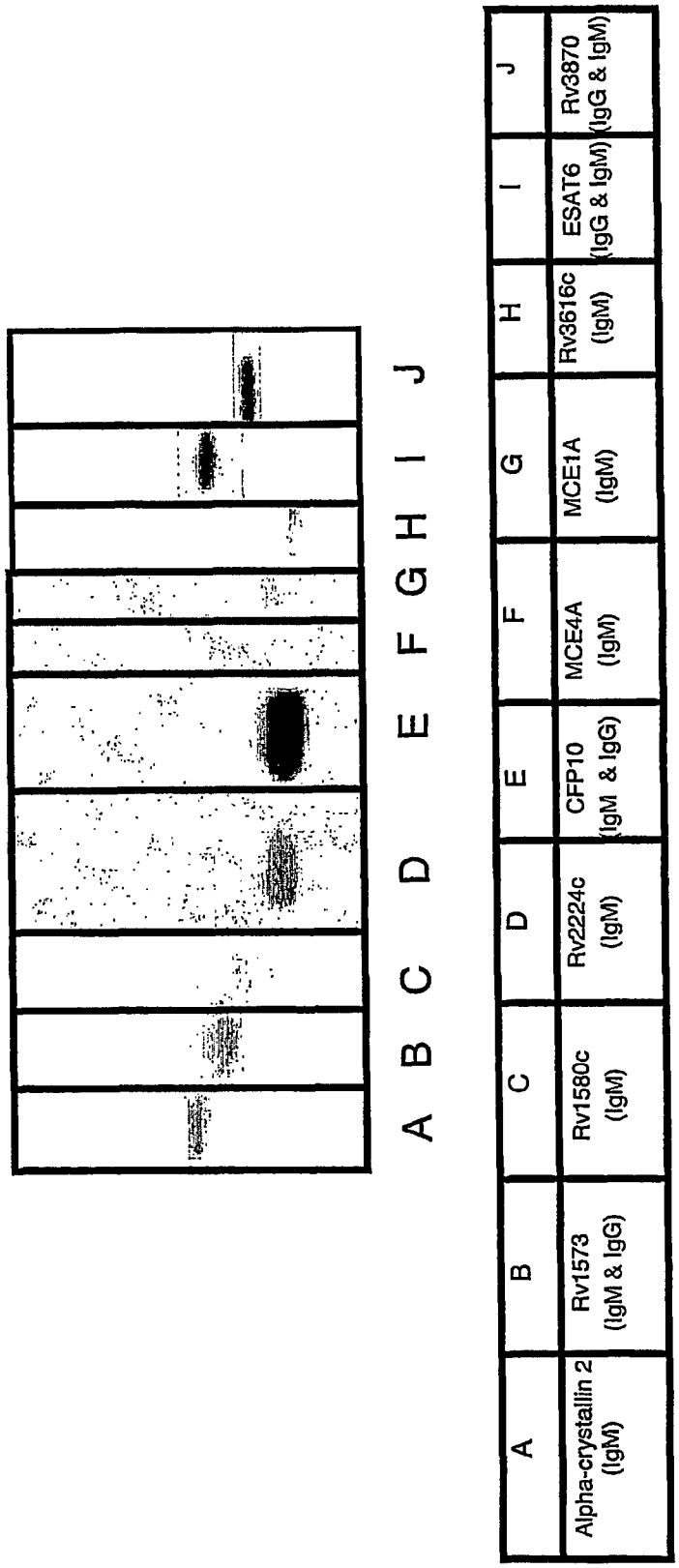
A B C D E F G H I J
| A | B | C | D | E | F | G | H | I | J |
|---|---|---|---|---|---|---|---|---|---|
| Alpha-crystallin 2 (IgM) | Rv1573 (IgM & IgG) | Rv1580c (IgM) | Rv2224c (IgM) | CFP10 (IgM & IgG) | MCE4A (IgM) | MCE1A (IgM) | Rv3616c (IgM) | ESAT6 (IgG & IgM) | Rv3870 (IgG & IgM) |
Figure 15. Summary of the western blot showing humoral immune response of *M. bovis* TB Infection in bovine samples (Samples were analysed for bovine IgM and IgG antibodies)

ASSAYS FOR DIAGNOSIS OF TUBERCULOSIS AND USES THEREOF

FIELD OF THE INVENTION

The invention relates to compounds for the diagnosis and herd profiling of mycobacterium infected or contaminated animals.

BACKGROUND TO THE INVENTION

Tuberculosis (TB), one of the most widespread infectious diseases, is the leading cause of death due to a single infectious agent among adults in the world. *Mycobacterium tuberculosis* is the most common cause of human TB.

However, an unknown proportion of cases of zoonotic tuberculosis are due to *M. bovis* with some due to *Mycobacterium avium*. Thus, infection of the animal population not only places a strain on economic resources but also presents a threat to human health. The requirement for successful diagnostic assays and potential vaccines has increased due to the recent rise in TB levels in the cattle population of countries such as Great Britain and the wild life reservoirs of the world (Hewinson et al 2003).

Great Britain performs some 4.6 million tests on bovine TB, costing the tax payer £88 m per annum (TB Conference *M. Bovis* IV Dublin 2005). Bovine TB varies regionally within GB, with the worst incidents seen in South Wales, Cornwall and Gloucestershire where 25% of all animals are infected. The incidence of TB is increasing at a rate of 2.5% per year in previously uninfected herds (TB Conference *M. Bovis* IV Dublin 2005).

In order to monitor and control the disease herd profiling is necessary. However, the methods currently used to monitor tuberculosis in animals suffer from a number of drawbacks. Nowadays, the disease control programmes for bovine TB carried out in most countries (i.e. US, Australia and GB etc.) are based on a test and removal strategy utilizing the intradermal skin test, which relies on PPD, a purified protein derivative of *M. bovis* strain AN5, to elicit an immune response in infected cattle (Caffrey, 1994; Monaghan et al., 1994).

In cattle, the intradermal skin tests currently used are the Caudal-fold Tuberculin Test (CFT) and the Comparative cervical tuberculin test (CCT). The Caudal-fold Tuberculin Test (CFT) is the Primary screening test used to identify cattle herds potentially infected with bovine tuberculosis. It measures the immune response to *Mycobacterium* Injecting Purified Protein Derivative (PPD) tuberculin (*M. bovis* AN5). If the animal's immune system recognizes the PPD, inflammatory cells (white blood cells) migrate to the injected site to help get rid of the foreign material (PPD). This cell mediated immune response may be recognized by swelling or discoloration at the site where PPD was injected. However, in 5% of cases, the CFT test may result in false-positive test results (due to exposure to or infection with other closely related bacteria, such as *M. avium* and *M. paratuberculosis*) or, in 15% of cases, in false-negative test results—where a very early stage of infection with bovine TB is not detected. As a follow up test to the CFT, the Comparative cervical tuberculin test (CCT) may be performed. The CCT test is performed in the cervical (neck) region and is a more definitive test designed to determine if a response noted on the CFT test is more likely due to infection with *M. avium* or *M. bovis* (injected with PPD avian and PPD bovine). CCT Test-suspect cattle are subjected to further testing using necropsy and further diagnostic testing.

Disease control based on the skin test can be complimented by the gamma-interferon test, which measures the animals T cell response when exposed to PPD material. The gamma-interferon test is utilised as a second line diagnostic for 'skin test positive' animals (reports suggest it is more sensitive, but sometimes less specific than skin test). It detects the cell-mediate immune response that develops following *M. bovis* infection (2 weeks).

The Gamma-Interferon test is not used as a primary test for mass screening on its own because it does not detect all skin test-positive infected animals; it is relatively expensive and is less specific than the CCT.

Due to their modes of action, the specificity of both the intradermal skin test and the gamma interferon test will always be an issue. The cross reactions induced by different mycobacteria strains and environmental mycobacteria such as *M. microti* and *M. africanum* and the conflicting requirements between specificity and sensitivity of the test antigens, all accrue to the difficulties in establishing a satisfactory serological protocol for bovine TB.

One of the problems associated with the complex antigenic nature of mycobacteria is the definition of those proteins which are important targets of the immune system and are thus likely present in large numbers of field samples. It is also important to recognize that there is regional variation in the infectious *M. bovis* strains.

An antibody assay developed using strain specific proteins could resolve both specificity and sensitivity issues.

A number of methods of discriminating between strains of tuberculosis have been suggested. U.S. Pat. No. 6,686,166B, WO 2004/083448A, US2004/0063923A, and U.S. Pat. No. 6,291,190B each describe 129 genetic marker sequences which are suggested for use in the identification of strains of mycobacteria. However, as described herein the mere identification of such markers does not equate with practical utility in a diagnostic method. Many markers are not expressed sufficiently to reliably be used in the identification of a strain. Further, as described further below, the amount of expression of individual markers varies considerably, not only between strains, but within strains geographically and within strains dependent on the stage of infection.

US2005/0272104A suggests the use of the PPD antigens ESAT-6 and CFP-10 in the detection of *Mycobacterium tuberculosis* in humans. In general however, antibody (Ab) tests based upon PPD tuberculins are characterised by a low discriminating power, with the distribution of the antibody titers between infected and non-infected animals being widely overlapping (Amadori et al. 1998). To date, a diagnostic test which accurately and reliably diagnoses the presence of tuberculosis infection has eluded the field.

SUMMARY OF THE INVENTION

As described herein, the present inventors have overcome a number of problems with the prior art diagnostic methods and have identified a number of polypeptides useful for the specific diagnosis and profiling of *Mycobacterium*. The inventors have found that each of the specific polypeptides is capable of eliciting a strong immune response in the absence of adjuvant. The characterized proteins/fragments which are immunogenic (or early antigens) and specific to one or other mycobacterial strains (See FIG. 1) can be used reliably for the diagnosis of tuberculosis infection or the discrimination between *Mycobacterium* strains.

Thus some of the polypeptides, as described below, are useful in the identification of *Mycobactrium bovis* infection. As described in the examples, such polypeptides elicit a strong immune response in serum from animals immunised with *Mycobacterium bovis*; however, when tested against the recombinant polypeptides, no such response was elicited in serum from rabbits immunised with avian or bovine PPD. It is recognized that due to the heterogeneity of the disease, no single antigen is present in all cases of infection. The use of a panel of immunogenic antigens with various strain specificity allows differentiation between *M bovis*, PPD (*M. bovis* AN5 and *M. avium*), *M. bovis* BCG and environmental mycobacteria based on antigen recognition patterns. This combination/multi peptide approach will allow strain specific diagnosis of infection together with herd profiling. It will also offer the possibility of regional disease monitoring/tracking.

The invention relates to the use of specific polypeptides, antibodies, or nucleic acid molecules for the detection of strain specific disease or mycobacterial challenge. The use of a multi-peptide approach combined with the selection of highly immunogenic peptide fragments both facilitate the sensitive and specific diagnosis of TB.

The polypeptides which may be used in the invention are SEQ ID NOs: 1-24 and variants and fragments thereof.

```
SEQ ID NO: 1 corresponds to residues 304-392 of
rv3616c (Mtb40):
ASTRQALRPRADGPVGAAAEQVGGQSQLVSAQGSQGMGGPVGMGGNHPSS

GASKGTTTKKYSEGAAAGTED

SEQ ID NO: 2 corresponds to Rv1573:
MTTTPARFNHLVTVTDLETGDRAVCDRDQVAETIRAWFPDAPLEVREALV

RLQAALNRHEHTGELEAFLRISVEHADAAGGDECGPAILAGRSGPEQAAI

NRQLGLAGDDEPDGDDTPPWSRMIGLGGGSPAEDER

SEQ ID NO: 3 corresponds to Rv1580c:
MAETPDHAELRRRIADMAFNADVGMATCKRCGDAVPYIILPNLQTGEPVM

GVADNKWKRANCPVDVGKPCPFLIAEGVADSTDDTIEVDQ

SEQ ID NO: 4 corresponds to Rv1585c:
MSRHHNIVIVCDHGRKGDGRIEHERCDLVAPIIWVDETQGWLPQAPAVAT

LLDDDNQPRAVIGLPPNESRLRPEMRRDGWVRLHWEFACLRYGAAGVRTC

EQRPVRVRNGDLQTLCENVPRLLTGLAGNPDYAPGFAVQSDAVVVANWLW

RTLCESDTPNKLRATPTRGSC

SEQ ID NO: 5 corresponds to Rv1572c:
NECSSAVHGQPRTNTFHHHEKLLRHNDEDNHDDP

SEQ ID NO: 6 corresponds to amino acid residues
84-192 of rv3870:
GLAGSTGGGGKKVPEINADRKEYLRYLAGLRTRVTSSATSQVAFFSYHAP

HPEDLLSIVGTQRQWSRPANADFYAATRIGIGDQPAVDRLLKPAVGGELA

AASAAPQPF

SEQ ID NO: 7 corresponds to Rv3875 (ESAT6):
TEQQWNFAGIEAAASAIQGNVTSIHSLLDEGKQSLTKLAAAWGGSGSEAY

QGVQQKWDATATELNNALQNLARTISEAGQAMASTEGNVTGMFA

SEQ ID NO: 8 corresponds to Rv3874 (CFP10):
AEMKTDAATLAQEAGNFERISGDLKTQIDQVESTAGSLQGQWRGAAGTAA

QAAVVRFQEAANKQKQELDEISTNIRQAGVQYSRADEEQQQALSSQMGF
```

SEQ ID NOS:9-11 correspond to amino acid residues 1-53, 120-196 and 319-93 of Rv0283 respectively.

```
SEQ ID NO: 9
MTNQQHDHDFDHDRRSFASRTPVNNNPDKVVYRRGFVTRHQVTGWRFVMR

RIA

SEQ ID NO: 10
EQLHPVLNLTSARLIVGRPVSPTTVKSTELDQFPRGNLIGIPGAPERWVQ

NTSTDANWTVCDGLNAPSRGGADGVG

SEQ ID NO: 11
QYYAVLPDGLQQISPVLAAILRNNNSYGLQQPPRLGADEVAKLPVSRVLD

TRRYPSEPVSLVDVTRDPVTCAYWSKP

SEQ ID NO: 12 corresponds to Rv0251c (A-crystallin
2):
MNNLALWSRPVWDVEPWDRWLRDFFGPAATTDWYRPVAGDFTPAAEIVKD

GDDAVVRLELPGIDVDKNVELDPGQPVSRLVIRGEHRDEHTQDAGDKDGR

TLREIRYGSFRRSFRLPAHVTSEAIAASYDAGVLTVRVAGAYKAPAETQA

QRIAITK:

SEQ ID NO: 13 corresponds to amino acid residues
32-137 of Rv2224c:
CIRVVGGRARMAEPKLGQPVEWTPCRSSNPQVKIPGGALCGKLAVPVDYD

RPDGDVAALALIRFPATGDKIGSLVINPGGPGESGIEAALGVFQTLPKRV

HER

SEQ ID NO: 14 corresponds to amino acid residues
322-380 of Mce1A:
TNSEILSGIGISLLSPLALATNGAAIGTGLVAGLIAPPLAVAANLAGALP

GIVGGAPNPYTYPEN

SEQ ID NO: 15 corresponds to amino acid residues
270-400 of Mce4A:
NRLEAPLKVTSDYSPVFGCLFKGIARGVKEFAPLIGVRKAGLFTSSSFVL

GAPSYTYPESLPIVNASGGPNCRGLPDIPTKQTGGSFYRAPFLVTDNALI

PYQPFTELQVDAPSTLQFLFNGAFAERDDF

SEQ ID NO: 16 corresponds to amino acid residues
72-111 of RpfC:
WDAVAQCESGGNWAANTGNGKYGGLQFKPATWAAFGGVG SEQ ID NO: 17 corresponds to amino acid residues
72-138 of RpfC:
WDAVAQCESGGNWAANTGNGKYGGLQFKPATWAAFGGVGNPAAASREQQI

AVANRVLAEQGLDAWP

SEQ ID NO: 18 corresponds to amino acid residues
460-486 of Rv2846c (efpA)
SRTLYLGGTTGPVKFMNDVQLAALDHA SEQ ID NO: 19 corresponds to MAP4244 (Avium
ESAT-6)
MDPTLSYNFGEIEHSVRQEIHTTSARFNAALDELRARIAPLQQLWTSEAA

TAYQAEQLKWHRSATALNEILIVLGDAVRDGAEEVADADRRAAGVWAR

SEQ ID NO: 20 corresponds to amino acid residues
179-223 of M4AP3779 (Avium Rv0283)
AVSEPGGHAAHSAGVTVIAGRPDSSGARAATLPSRQALLADRDGT
```

-continued

SEQ ID NO: 21 corresponds to amino acid residues
181-287 of MAPP1522
AQAAALGEATGRGAGTVAADATAPPSGIISQLLEALGNASRGYMDFWDQV

LNTLTGSPLAGTTWQNTFGILADIGRFSTVANDSMSPINLAMTEFKMFYK

LPVEGLD

SEQ ID NO: 22 corresponds to MAP1607c (Avium RPFc)
MFSPAEMAVFADRRHISRHFRIGNALATRAEILDMTNLCKLLVKSVVVGG

FVAASMASSTGVVSAEPTPNWDAIAQCESGGNWHANTGNGEYGGLQFKPA

TWARYGGVGNPAAASREQQIAVANRVFAEEGVEPWPKCGAQSGLPIGWYS

HPAQGIKQIINGLIQAAVPR

SEQ ID NO: 23 corresponds to 3614c
VDLPGNDFDSNDFDAVDLWGADGAEGWTADPIIGVGSAATPDTGPDLDNA

HGQAETDTEQEIALFTVTNPPRTVSVSTLMDGRIDHVELSARVAWMSESQ

LASEILVIADLARQKAQSAQYAFILDRMSQQVDADEHRVALLRKTVGETW

GLPSPEEAAAAEAEVFATRYSDDCPAPDDESDPW

The inventors have found that the peptides having amino acid sequences SEQ ID NO: 1 to SEQ ID NO: 23 each elicit strong immune response in serum from animals immunised with mycobacterial strains.

Of these, the peptides having amino acid sequences SEQ ID NO: 1 to SEQ ID NO: 8 each elicit strong immune responses in serum from animals immunised with Mycobacterial bovis. With the exception of Rv1572c (SEQ ID NO: 5), these antigens are not present in either environmental strains of *Mycobacterium* or avian PPD strains and thus in combinations of two or more allow reliable specific detection of the presence of or exposure to *Mycobacterium bovis* in an animal or sample.

Accordingly, in a first aspect of the invention, there is provided a method of diagnosis of tuberculosis in an animal, the method comprising the steps:

- providing a biological sample from said animal; and determining the presence or absence of two or more polypeptides, or the presence or absence of an immune response to said polypeptides,
- wherein said polypeptides are selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6, SEQ ID NO:7, SEQ ID NO: 8 or SEQ ID NO:23; or a variant or fragment thereof in the biological sample;
- wherein where one of said polypeptides has amino acid sequence SEQ ID NO: 7 or SEQ ID NO: 8, the presence of at least one polypeptide selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6 or SEQ ID NO: 23, or an immune response thereto, is determined;

wherein the presence of two or more of said polypeptides or the presence of an immune response to said polypeptides is indicative of the presence of tuberculosis infection in the animal.

In one embodiment of the first aspect of the invention, the method comprises the steps:

- providing a biological sample from said animal; and determining the presence or absence of two or more polypeptides, or the presence or absence of an immune response to said polypeptides,
- wherein said polypeptides are selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6, SEQ ID NO:7, or SEQ ID NO:8; or a variant or fragment thereof in the biological sample;
- wherein where one of said polypeptides has amino acid sequence SEQ ID NO: 7 or SEQ ID NO: 8, the presence of at least one polypeptide selected from the polypeptides having the amino acid sequence shown as any one of SEQ ID NO:1, SEQ ID NO:2, SEQ ID NO:3, SEQ ID NO:4, SEQ ID NO:5, or SEQ ID NO: 6, or an immune response thereto, is determined;

wherein the presence of two or more of said polypeptides or the presence of an immune response to said polypeptides is indicative of the presence of tuberculosis infection in the animal.

The methods of the invention may be used with any animal, for example any mammal, including humans or bird. In one embodiment, the animal is a mammal. In one particular embodiment, the mammal is a non-human mammal.

In a second aspect, the present invention provides an assay for the detection of the presence of *Mycobacterium*, for example *Mycobacterium bovis*, in a biological sample, said method comprising the steps:

- providing a biological sample; and determining the presence or absence of two or more polypeptides, or the presence of an immune response to said polypeptides,
- wherein said polypeptides are selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6, SEQ ID NO:7, SEQ ID NO: 8, or SEQ ID NO:23; or a variant or fragment thereof in the biological sample;
- wherein where one of said polypeptides has amino acid sequence SEQ ID NO: 7 or SEQ ID NO: 8, the presence of at least one polypeptide selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6, or SEQ ID NO: 23, or an immune response thereto, is determined;

wherein the presence of one or more of said polypeptides, or an immune response thereto, is indicative of the presence of *Mycobacterium* in the biological sample.

In one embodiment of the second aspect of the invention, the method comprises the steps:

- providing a biological sample; and determining the presence or absence of two or more polypeptides, or the presence of an immune response to said polypeptides,
- wherein said polypeptides are selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6, SEQ ID NO:7, or SEQ ID NO: 8; or a variant or fragment thereof in the biological sample;
- wherein where one of said polypeptides has amino acid sequence SEQ ID NO: 7 or SEQ ID NO: 8, the presence of at least one polypeptide selected from the polypeptides having the amino acid sequence shown as any one of SEQ ID NO:1, SEQ ID NO:2, SEQ ID NO:3, SEQ ID NO:4, SEQ ID NO:5, or SEQ ID NO: 6, or an immune response thereto, is determined; wherein the presence of one or more of said polypeptides, or an immune response thereto, is indicative of the presence of *Mycobacterium* in the biological sample.

The inventors have found that a particularly strong response is elicited to the antigen Rv3616c in serum exposed to *Mycobacterium bovis*. Accordingly, in one embodiment of the first and second aspects of the invention, the method comprises determining the presence of a polypeptide having the amino acid sequence shown as SEQ ID NO: 1, or a variant or fragment thereof, or an immune response thereto.

Although Rv3616c elicits a particularly strong immune response, this antigen is also present in bovine PPD. Similarly, ESAT6, CFP10 and Rv3870 can also be present in both *Mycobacterium bovis* and bovine PPD and thus in animals which may have been exposed to PPD, for example, domesticated farm animals, the use of these antigens in isolation may not enable discrimination between exposure to bovine PPD and infection with *Mycobacterium bovis*.

However, Rv573, Rv1580c, Rv585c and Rv1572c are not expressed in bovine PPD and thus, in one embodiment of the invention, the method comprises determining the presence of at least one, for example two, three or four of the polypeptides having the amino acid sequence shown as SEQ ID NO: 2, 3, 4, or 5, or an immune response thereto.

In an embodiment, the method comprises determining the presence of a polypeptide having the amino acid sequence shown as SEQ ID NO: 5, or an immune response thereto.

In a particular embodiment of the invention, the method comprises determining the presence of:
(i) at least one, for example two, three or four of the polypeptides having the amino acid sequence shown as SEQ ID NOS: 2, 3, 4, or 5, or an immune response thereto; and
(ii) at least one, for example two, three or four of the polypeptides having the amino acid sequence shown as SEQ ID NOS: 1, 6, 7, 8 and 23, or an immune response thereto.

In another particular embodiment of the invention, the method comprises determining the presence of:
(i) at least one, for example two, three or four of the polypeptides having the amino acid sequence shown as SEQ ID NOS: 2, 3, 4, or 5, or an immune response thereto; and
(ii) at least one, for example two, three or four of the polypeptides having the amino acid sequence shown as SEQ ID NOS: 1, 6, 7, and 8, or an immune response thereto.

In one embodiment of the first or second aspects of the invention, the determination of the presence of said polypeptides, or an immune response thereto, is indicative of the presence of bovine tuberculosis.

Where the selected polypeptide is present in the wild-type *Mycobacterium* but not in strains used for vaccines, such as *Myobacterium bovis bacillus* Calmette-Guerin (BCG), the invention may be used to discriminate between infected animals and vaccinated animals. This will be particularly valuable in the control of tuberculosis in herds of animals.

Accordingly, in a third aspect of the invention, there is provided a method of determining whether an animal is infected with tuberculosis or vaccinated against tuberculosis, said method comprising the steps:
(a) providing a biological sample from said animal; and
(b) determining in the biological sample:
  (i) the presence of a polypeptide having the amino acid sequence shown as SEQ ID NO:1 or a variant or fragment thereof, or the presence of an immune response thereto
  (ii) the presence of one or more of the polypeptides having the amino acid sequence shown as any one of SEQ ID NO:2, SEQ ID NO:3, and SEQ ID NO:4 or a variant or fragment thereof, or the presence of an immune response thereto, and
  (iii) the presence of one or more of the polypeptides having the amino acid sequence shown as SEQ ID NO: 6, SEQ ID NO:7 or SEQ ID NO:8, or a variant or fragment thereof, or the presence of an immune response thereto;

wherein the identification of the presence of (i), (ii) and (iii) in the biological sample is indicative of the presence of infection of the animal with tuberculosis; and
wherein the identification of the presence of (i) and (ii) combined with the identification of the absence of each of polypeptides having the amino acid sequence shown as SEQ ID NO: 6, SEQ ID NO:7 and SEQ ID NO:8 respectively in the biological sample, and the absence of an immune response to each of the polypeptides having the amino acid sequence shown as SEQ ID NO: 6, SEQ ID NO:7 and SEQ ID NO:8 respectively in the biological sample is indicative of vaccination of the animal with a vaccine.

Of particular utility in this aspect of the invention is the identification of the presence of one or more polypeptides having amino acid sequences SEQ ID NOS: 6, 7 and 8, or of a immune response to said polypeptides. These polypeptides are not present in BCG vaccines and thus detection of their presence, or of an immune response to the polypeptides, is indicative of a source of antigen, such as infection, other than such vaccination. Thus the presence of one or more of said polypeptides having SEQ ID NOS: 6, 7 or 8, or the presence of an immune response thereto, is indicative that the animal is infected with tuberculosis.

In the methods of the invention, the inventors have determined that, by testing for presence of a plurality of antigens, the sensitivity of the test is greatly improved and an accurate identification of the source of *Mycobacterium* may be obtained.

Thus in one embodiment, the method comprises determining the presence or absence of three or more, for example four, five, six, seven, eight or nine, polypeptides selected from the polypeptides having the amino acid sequence shown as any one of SEQ ID NO:1, SEQ ID NO:2, SEQ ID NO:3, SEQ ID NO:4,
SEQ ID NO:5, SEQ ID NO: 6, SEQ ID NO:7, SEQ ID NO: 8 or SEQ ID NO:23; or a variant or fragment thereof, or the presence or absence of an immune response to said polypeptides.

In another embodiment, the method comprises determining the presence or absence of three or more, for example four, five, six, seven, or eight polypeptides selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6, SEQ ID NO:7, or SEQ ID NO: 8; or a variant or fragment thereof, or the presence or absence of an immune response to said polypeptides.

Furthermore, as well as determining the strong immunogenic nature of the antigens corresponding to SEQ ID NO: 1-SEQ ID NO: 8 and SEQ ID NO: 23, the inventors have also identified a number of Mycobacterial antigens which are present in environmental *Mycobacterium* or avian PPD strains but not in bovine strains and some antigens which are expressed in environmental or avian PPD strains as well as bovine PPD and in *Mycobacterium bovis* (see FIG. 1).

The identification of the strong immunogenic response provoked by these antigens allows them to be used in the assays of the invention to further discriminate between sources of antigen. Accordingly, in one embodiment of the methods of the first or second aspects of the invention, the presence or absence of one or more, for example two, three, four, five, six, seven, eight, nine or ten polypeptides selected from the polypeptides having the amino acid sequence shown as any one of SEQ ID NO: 9, SEQ ID NO: 10, SEQ ID NO: 11, SEQ ID NO:12, SEQ ID NO:13, SEQ ID NO:14, SEQ ID NO:15, SEQ ID NO: 16, SEQ ID NO:17, or SEQ ID NO: 18 or a variant or fragment thereof, or the presence or absence of an immune response to said polypeptides, is determined. These antigens are expressed in environmental or avian PPD strains as well as bovine PPD and in *Mycobacterium bovis*.

In another embodiment the presence or absence of one or more, for example two, three, or four polypeptides selected from the polypeptides having the amino acid sequence shown as any one of SEQ ID NO: 19, SEQ ID NO: 20, SEQ ID NO: 21, SEQ ID NO:22; or a variant or fragment thereof, or the presence or absence of an immune response to said polypeptides, is determined. These antigens are present in environmental *Mycobacterium* or avian PPD strains but not in bovine strains.

In the present specification, unless the context demands otherwise, references to tuberculosis should be taken to refer to any tuberculosis, for example human tuberculosis, non-human animal tuberculosis, avian tuberculosis or a para-tuberculosis disease, such as Johne's disease.

Unless the context demands otherwise, reference to *Mycobacterium* should be taken to refer to any *Mycobacterium*.

In one embodiment, the *Mycobacterium* is *Mycobacterium tuberculosis*.

In another embodiment the *Mycobacterium* is *Mycobacterium bovis*.

In another embodiment, the *Mycobacterium* is *Mycobacterium avium*.

In another embodiment, the *Mycobacterium* is *Mycobacterium paratuberculosis*.

Any suitable biological sample may be used in the methods of the invention. Suitable biological samples include but are not limited to whole blood, serum, plasma, saliva, cerebrospinal fluid, urine and tissue samples.

In the methods of the invention, the presence of particular polypeptides or an immune response thereto may be determined using any means known in the art, either directly or indirectly. For example, in one embodiment, the presence of the polypeptide in the sample is determined; alternatively or additionally the presence of an antibody specific to said polypeptide is determined; alternatively or additionally the presence of an nucleic acid encoding said antibody or said polypeptide is determined.

The identification by the inventors of mycobacterial antigens which are particularly immunogenic enables the use of these polypeptides in the preparation of novel vaccines against tuberculosis.

Accordingly, in a fourth aspect of the present invention, there is provided a vaccine comprising two or more, for example three, four, five, six, seven, eight, nine, ten, eleven, twelve, thirteen, fourteen, fifteen, sixteen, seventeen, eighteen or nineteen of the polypeptides selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6, SEQ ID NO:7, SEQ ID NO:8, SEQ ID NO: 9, SEQ ID NO: 10, SEQ ID NO: 11, SEQ ID NO: 12, SEQ ID NO:13, SEQ ID NO:14, SEQ ID NO:15, SEQ ID NO: 16, SEQ ID NO: 17, SEQ ID NO: 18 or SEQ ID NO:23; or a variant or fragment thereof.

In one embodiment the vaccine is a vaccine against tuberculosis.

In an alternative embodiment of the fourth aspect of the invention, one or more of said polypeptides are used in a vaccine as an adjuvant.

In a fifth aspect of the invention, there is provided a method of providing immunity in a animal against tuberculosis, the method comprising administering to said animal a vaccine according to the fourth aspect of the invention.

In a sixth aspect of the invention, there is provided the use of two or more, for example three, four, five, six, seven, eight, nine, ten, eleven, twelve, thirteen, fourteen, fifteen, sixteen, seventeen, eighteen or nineteen of the polypeptides selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6, SEQ ID NO:7, SEQ ID NO:8, SEQ ID NO: 9, SEQ ID NO: 10, SEQ ID NO: 11, SEQ ID NO: 12, SEQ ID NO:13, SEQ ID NO:14, SEQ ID NO:15, SEQ ID NO: 16, SEQ ID NO: 17, SEQ ID NO: 18 or SEQ ID NO:23; or variants or fragments thereof in the preparation of a vaccine against tuberculosis.

In the vaccine of the fourth aspect of the invention or the use of the sixth aspect of the invention, where one of said polypeptides has amino acid sequence SEQ ID NO: 7 or SEQ ID NO: 8, the vaccine comprises at least one polypeptide selected from the polypeptides having the amino acid sequence shown as any one of SEQ ID NO:1 to SEQ ID NO: 6, SEQ ID NO: 9 to SEQ ID NO: 18 or SEQ ID NO: 23.

In a seventh aspect, the invention provides a diagnostic kit for the diagnosis of the presence of tuberculosis in a biological sample, said kit comprising: two or more of the polypeptides selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6, SEQ ID NO:7, SEQ ID NO:8, or SEQ ID NO: 23; or a variant or fragment thereof;
wherein where one of said polypeptides has amino acid sequence SEQ ID NO: 7 or SEQ ID NO: 8, the kit comprises at least one polypeptide selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6 or SEQ ID NO: 23.

In an embodiment of the seventh aspect, the invention provides a diagnostic kit for the diagnosis of the presence of tuberculosis in a biological sample, said kit comprising: two or more of the polypeptides selected from the polypeptides having the amino acid sequence shown as any one of SEQ ID NO:1, SEQ ID NO:2, SEQ ID NO:3, SEQ ID NO:4, SEQ ID NO:5, SEQ ID NO: 6, SEQ ID NO:7, or SEQ ID NO:8; or a variant or fragment thereof;
wherein where one of said polypeptides has amino acid sequence SEQ ID NO: 7 or SEQ ID NO: 8, the kit comprises at least one polypeptide selected from the polypeptides having the amino acid sequence shown as any one of SEQ ID NO:1, SEQ ID NO:2, SEQ ID NO:3, SEQ ID NO:4, SEQ ID NO:5, or SEQ ID NO: 6.

In an eighth aspect of the invention, there is provided a diagnostic kit for the diagnosis of the presence of tuberculosis in a biological sample, said kit comprising: two or more antibody molecules, wherein each antibody molecule is independently selected from the group comprising an antibody molecule with binding specificity for a polypeptide having the amino acid sequence shown as SEQ ID NO:1 or a variant or fragment thereof, a polypeptide having the amino acid sequence shown as SEQ ID NO:2 or a variant or fragment thereof, a polypeptide having the amino acid sequence shown as SEQ ID NO:3 or a variant or fragment thereof, a polypeptide having the amino acid sequence shown as SEQ ID NO:4, or a variant or fragment thereof, a polypeptide having the amino acid sequence shown as SEQ ID NO:5 or a variant or fragment thereof, a polypeptide having the amino acid sequence shown as SEQ ID NO: 6 or a variant or fragment thereof, a polypeptide having the amino acid sequence shown as SEQ ID NO:7 or a variant or fragment thereof, a polypeptide having the amino acid sequence shown as SEQ ID NO:8 or a variant or fragment thereof, or a polypeptide having the amino acid sequence shown as SEQ ID NO:23 or a variant or fragment thereof;

wherein where one of said polypeptides has amino acid sequence SEQ ID NO: 7 or SEQ ID NO: 8, the kit comprises at least one antibody molecule with binding specificity for a polypeptide having amino acid sequence shown as SEQ ID NO:1, SEQ ID NO:2, SEQ ID NO:3, SEQ ID NO:4, SEQ ID NO:5, SEQ ID NO: 6 or SEQ ID NO: 23.

In one embodiment of the eighth aspect of the invention, the kit comprises: two or more antibody molecules, wherein each antibody molecule is independently selected from the group comprising an antibody molecule with binding specificity for a polypeptide having the amino acid sequence shown as SEQ ID NO:1 or a variant or fragment thereof, a polypeptide having the amino acid sequence shown as SEQ ID NO:2 or a variant or fragment thereof, a polypeptide having the amino acid sequence shown as SEQ ID NO:3 or a variant or fragment thereof, a polypeptide having the amino acid sequence shown as SEQ ID NO:4, or a variant or fragment thereof, a polypeptide having the amino acid sequence shown as SEQ ID NO:5 or a variant or fragment thereof, a polypeptide having the amino acid sequence shown as SEQ ID NO: 6 or a variant or fragment thereof, a polypeptide having the amino acid sequence shown as SEQ ID NO:7 or a variant or fragment thereof, or a polypeptide having the amino acid sequence shown as SEQ ID NO:8 or a variant or fragment thereof;
wherein where one of said polypeptides has amino acid sequence SEQ ID NO: 7 or SEQ ID NO: 8, the kit comprises at least one antibody molecule with binding specificity for a polypeptide having amino acid sequence shown as SEQ ID NO:1, SEQ ID NO:2, SEQ ID NO:3, SEQ ID NO:4, SEQ ID NO:5, or SEQ ID NO: 6.

As described above, the inventors have found that Rv3616c elicits a particularly strong response in serum exposed to *Mycobacterium bovis*.

Accordingly, in a further embodiment of the invention, there is provided a method of diagnosis of tuberculosis in an animal, the method comprising the steps:
providing a biological sample from said animal; and determining the presence or absence of a polypeptide having the amino acid sequence shown as SEQ ID NO:1, or a variant or fragment thereof, or the presence or absence of an immune response thereto, in the biological sample;
wherein the presence of said polypeptide or an immune response thereto is indicative of the presence of tuberculosis infection in the animal.

Another aspect of the invention is an assay method for the detection of the presence of *Mycobacterium* in a biological sample, said method comprising the steps:
providing a biological sample; and determining the presence or absence of a polypeptide having the amino acid sequence shown as SEQ ID NO:1, or a variant or fragment thereof, or an immune response thereto, in the biological sample;
wherein the presence of said polypeptide, or an immune response thereto, is indicative of the presence of *Mycobacterium* in the biological sample.

A further aspect comprises a vaccine wherein the vaccine comprises a polypeptide having the amino acid sequence SEQ ID NO:1; or a variant or fragment thereof.

A further aspect comprises a diagnostic kit for the diagnosis of the presence of tuberculosis in a biological sample, said kit comprising:
a polypeptide having the amino acid sequence shown as SEQ ID NO:1 or a variant or fragment thereof.

Preferred features of each aspect of the invention are as for each of the other aspects mutatis mutandis.

DETAILED DESCRIPTION

Polypeptides, Variants and Fragments

As described above, the inventors have identified a number of tuberculosis antigens which may be used in the diagnosis of tuberculosis, the differentiation between strains of *Mycobacteria*, and preparation of vaccines. In one embodiment of the invention, the polypeptides for use in the invention consist of polypeptides consisting of the amino acid sequence shown as any one of SEQ ID NO:1 to SEQ ID NO: 23.

However, the present invention is not limited to the use of polypeptides having such specific sequences of the polypeptides or antibodies disclosed herein but also extends to variants thereof. Thus, variant polypeptide sequences in which one or more amino acid residues are modified may also be used as the polypeptides in the invention. For example such variants may be useful in the preparation of vaccines or the raising of antibodies which may be used in kits of the invention. Modifications may involve insertion, addition, deletion and/or substitution of one or more amino acids. The modified amino acid residues in the amino acid sequences of the variant are preferably 30% or less, more preferably 20% or less, most preferably 10% or less, within the entire polypeptide. Such variants may be provided using the teaching of the present application and techniques known in the art. Preferably such variants involve the insertion, addition, deletion and/or substitution of 15 or fewer amino acids, more preferably of 10 or fewer, even more preferably of 5 or fewer, most preferably of 1 or 2 amino acids only.

Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions may include but are not limited to Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu.

In preferred embodiments, a variant or fragment retains the immune reactivity of the polypeptide having the amino acid sequence shown as any one of SEQ ID NO:1 to SEQ ID NO: 23, of which it is a variant or fragment.

For the avoidance of any doubt, in the present application, where reference is made to the presence of two or more polypeptides selected from a list, for example two or more of the polypeptides selected from the polypeptides having the amino acid sequence shown as any one of SEQ ID NO:1, SEQ ID NO:2, SEQ ID NO:3, etc, it should be understood that reference is being made to at least one (first) polypeptide having one of the recited amino acid sequences and at least one (second) polypeptide having another of the recited amino acid sequences, which is different from the amino acid sequence of the first polypeptide.

Furthermore, for the avoidance of any doubt, in the present application, unless the context demands otherwise, where reference is made to the determination of the presence or absence of two or more polypeptides selected from a list, or the presence or absence of an immune response thereto, it should be understood that such a statement encompasses the determination of the presence or absence of two or more of said polypeptides selected from the list or the determination of the presence or absence of an immune response to two or more of said polypeptides or indeed a mixture thereof i.e. the determination of the presence or absence of one or more polypeptides selected from the list combined with the determination of an immune response to one or more other polypeptides selected from the list.

Antibody Molecules

In the context of the present invention, an "antibody molecule" should be understood to refer to an immunoglobulin or part thereof or any polypeptide comprising a binding domain which is, or is homologous to, an antibody binding domain. Antibodies include but are not limited to polyclonal, monoclonal, monospecific, polyspecific antibodies and fragments thereof and chimeric antibodies comprising an immunoglobulin binding domain fused to another polypeptide.

Intact (whole) antibodies comprise an immunoglobulin molecule consisting of heavy chains and light chains, each of which carries a variable region designated VH and VL, respectively. The variable region consists of three complementarity determining regions (CDRs, also known as hypervariable regions) and four framework regions (FR) or scaffolds. The CDR forms a complementary steric structure with the antigen molecule and determines the specificity of the antibody.

Fragments of antibodies may retain the binding ability of the intact antibody and may be used in place of the intact antibody. Accordingly, for the purposes of the present invention, unless the context demands otherwise, the term "antibodies" should be understood to encompass antibody fragments. Examples of antibody fragments include Fab, Fab, F(ab')2, Fd, dAb, and Fv fragments, scFvs, bispecific scFvs, diabodies, linear antibodies (see U.S. Pat. No. 5,641,870, Example 2 Zapata et al., Protein Eng 8 (10): 1057-1062 [1995]); single-chain antibody molecules; and multispecific antibodies formed from antibody fragments.

The Fab fragment consists of an entire L chain (VL and CL), together with VH and CH1. Fab'fragments differ from Fab fragments by having additional few residues at the carboxy terminus of the CH1 domain including one or more cysteines from the antibody hinge region. The F (ab') 2 fragment comprises two disulfide linked Fab fragments.

Fd fragments consist of the VH and CH1 domains.

Fv fragments consist of the VL and VH domains of a single antibody.

Single-chain Fv fragments are antibody fragments that comprise the VH and VL domains connected by a linker which enables the scFv to form an antigen binding site. (see Pluckthun in The Pharmacology of Monoclonal Antibodies, vol. 113, Rosenburg and Moore eds., Springer-Verlag, New York, pp. 269-315 (1994).

Diabodies are small antibody fragments prepared by constructing scFv fragments (see preceding paragraph) with short linkers (about 5-10 residues) between the VH and VL domains such that inter-chain but not intra-chain pairing of the V domains is achieved, resulting in a multivalent fragment, i.e. a fragment having two antigen-binding sites (see, for example, EP 404 097; WO 93/11161; and Hollinger et al., Proc. Natl. Acad. Sci. USA, 90: 6444-6448 (1993))

Further encompassed by fragments are individual CDRs. The CDRs may be carried in a framework structure comprising an antibody heavy or light chain sequence or part thereof Preferably such CDRs are positioned in a location corresponding to the position of the CDR(s) of naturally occurring VH and VL domains. The positions of such CDRs may be determined as described in Kabat et al, Sequences of Proteins of Immunological Interest, US Dept of Health and Human Services, Public Health Service, Nat'l Inst. of Health, NIH Publication No. 91-3242, 1991 Furthermore, modifications may alternatively or additionally be made to the Framework Regions of the variable regions. Such changes in the framework regions may improve stability and reduce immunogenicity of the antibody.

The antibody molecules for use in the present invention extends, for example, to any other antibody which specifically binds a polypeptide identified herein as inducing a strong immune response i.e. an antibody molecule which retains binding specificity for a polypeptide consisting of amino acid sequence shown as any one of SEQ ID NOs:1 to 24.

Antibodies for use in the invention herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81: 6851-6855 (1984)). Chimeric antibodies of interest herein include "primatized" antibodies comprising variable domain antigen-binding sequences derived from a non-human primate (e.g. Old World Monkey, Ape etc), and human constant region sequences.

Antibody molecules for use in the present invention may be produced in any suitable way, either naturally or synthetically. Such methods may include, for example, traditional hybridoma techniques (Kohler and Milstein (1975) Nature, 256: 495-499), recombinant DNA techniques (see e.g. U.S. Pat. No. 4,816,567), or phage display techniques using antibody libraries (see e.g. Clackson et al. (1991) Nature, 352: 624-628 and Marks et al. (1992) Bio/Technology, 10: 779-783). Other antibody production techniques are described in Antibodies: A Laboratory Manual, eds. Harlow et al., Cold Spring Harbor Laboratory, 1988.

Traditional hybridoma techniques typically involve the immunisation of a mouse or other animal with an antigen in order to elicit production of lymphocytes capable of binding the antigen. The lymphocytes are isolated and fused with a myeloma cell line to form hybridoma cells which are then cultured in conditions which inhibit the growth of the parental myeloma cells but allow growth of the antibody producing cells. The hybridoma may be animal to genetic mutation, which may or may not alter the binding specificity of antibodies produced.

Synthetic antibodies can be made using techniques known in the art (see, for example, Knappik et al, J. Mol. Biol. (2000) 296, 57-86 and Krebs et al, J. Immunol. Meth. (2001) 2154 67-84.

Modifications may be made in the VH, VL or CDRs of the antibody molecules, or indeed in the FRs using any suitable technique known in the art. For example, variable VH and/or VL domains may be produced by introducing a CDR, e.g. CDR3 into a VH or VL domain lacking such a CDR. Marks et al. (1992) Bio/Technology, 10: 779-783 describe a shuffling technique in which a repertoire of VH variable domains lacking CDR3 is generated and is then combined with a CDR3 of a particular antibody to produce novel VH regions. Using analogous techniques, novel VH and VL domains comprising CDR derived sequences of the present invention may be produced.

Alternative techniques of producing antibodies for use in the invention may involve random mutagenesis of gene(s)

encoding the VH or VL domain using, for example, error prone PCR (see Gram et al, 1992, P.N.A.S. 89 3576-3580. Additionally or alternatively, CDRs may be targeted for mutagenesis e.g. using the molecular evolution approaches described by Barbas et al 1991 PNAS 3809-3813 and Scier 1996 J Mol Biol 263 551-567.

Having produced such variants, antibodies and fragments may be tested for binding to *Mycobacterium bovis*.

The antibodies for use in the invention may comprise further modifications. For example the antibodies can be glycosylated, pegylated, or linked to albumin or a nonproteinaceous polymer.

Antibodies for use in the invention may be labelled. Labels which may be used include radiolabels, enzyme labels such as horseradish peroxidase or alkaline phosphatase, or biotin.

Nucleic Acid

Nucleic acid for use in the present invention may comprise DNA or RNA. It may be produced recombinantly, synthetically, or by any means available to those in the art, including cloning using standard techniques.

The nucleic acid may be inserted into any appropriate vector. A vector comprising a nucleic acid of the invention forms a further aspect of the present invention. In one embodiment the vector is an expression vector and the nucleic acid is operably linked to a control sequence which is capable of providing expression of the nucleic acid in a host cell. A variety of vectors may be used.

For example, suitable vectors may include viruses (e.g. vaccinia virus, adenovirus, etc.), baculovirus); yeast vectors, phage, chromosomes, artificial chromosomes, plasmids, or cosmid DNA.

The vectors may be used to introduce the nucleic acids of the invention into a host cell. A wide variety of host cells may be used for expression of the nucleic acid of the invention. Suitable host cells for use in the invention may be prokaryotic or eukaryotic. They include bacteria, e.g. *E. coli*, yeast, insect cells and mammalian cells. Mammalian cell lines which may be used include Chinese hamster ovary cells, baby hamster kidney cells, NSO mouse melanoma cells, monkey and human cell lines and derivatives thereof and many others.

A host cell strain that modulates the expression of, modifies, and/or specifically processes the gene product may be used. Such processing may involve glycosylation, ubiquiination, disulfide bond formation and general post-translational modification.

For further details relating to known techniques and protocols for manipulation of nucleic acid, for example, in preparation of nucleic acid constructs, mutagenesis, sequencing, introduction of DNA into cells and gene expression, and analysis of proteins, see, for example, Current Protocols in Molecular Biology, 5th ed., Ausubel et al. eds., John Wiley & Sons, 2005 and, Molecular Cloning: a Laboratory Manual: $3^{rd}$ edition Sambrook et al., Cold Spring Harbor Laboratory Press, 2001.

Diagnostic Methods, Assays and Kits

The invention may be used in the diagnosis of a variety of conditions and disorders associated with tuberculosis. These include *mycobacterium bovis, mycobacterium avium* and human mycobacterium and para-tuberculosis diseases such as Johne's disease.

In using the methods of the invention to identify the infection with a mycobacterial strain, either as current or previous infection, the presence or absence of immunogenic polypeptides, or the presence or absence of an immune response to said polypeptides is determined from a biological sample. Any suitable biological sample may be used. For example, the biological sample may be a biological fluid, such as sputum, saliva, plasma, blood, urine or sperm, or a tissue, such as a biopsy of a tissue. Diagnostic and assay means of detecting the presence of polypeptides or an immune responses to said polypeptides are known in the art. For example, the presence of the polypeptides any be detected by use of antibodies specific to said polypeptides. Alternatively, using standard techniques in the art, the presence of nucleic acids encoding the polypeptide or indeed an antibodyspecific to said polypeptide may be used. Further, the presence of antibodies specific to said polypeptides may be used to determine the presence of an immune response to said polypeptide.

Techniques which may be employed include but are not limited to ELISA, Immunohistochemistry, Electron Microscopy, Latex agglutination, Immuno Blotting, immunochromatography, immunochips, lateral flow immunoassays and Dip Stick Immuno testing.

The ELISA test (enzyme linked immunoenzymatic assay) is frequently used for serological diagnosis. This method allows the identification and quantification of antigens or antibodies in biological fluids. The conventional ELISA consists in the detection of the complex antibody-antigen by a second antibody (against the antibody that reacts with the antigen) conjugated to an enzymatic activity (peroxidase, alkaline phosphatase and others).

In the latex agglutination assay, the antigen preparation is affixed to latex beads. The biological sample is then incubated directly on a slide with the latex particles. In a short time the reaction is examined for the presence of cross-linked, or agglutinated latex particles indicating the presence of antibodies to polypeptides in the sample.

Immunochips may used to determine the presence of the specific *Mycobacterium* antigens. Generally, the specific antibodies to the antigens are immobilised on a transducer, e.g. electrodes, caloric meter, piezoelectric crystal, surface plasmon resonance transducer, surface acoustic resonance transducer or other light detecting device. The binding of antigens in the biological sample to the immobilised specific antibody is detected by a change in electric signal.

As described above, the presence of the immunogenic antigens may be detected by detecting nucleic acids encoding the antigen or encoding antibodies raised against the antigen. Such techniques are well known in the art. For example, where large amounts of DNA are available, genomic DNA may be used directly. Alternatively, the region of interest is cloned into a suitable vector and grown in sufficient quantity for analysis. The nucleic acid may be amplified by conventional techniques, such as the polymerase chain reaction (PCR) (Saiki, et al. (1985) Science 239:487). Primers may be used to amplify sequences encoding the polypeptide of interest. Optionally, a detectable label, for example a fluorochrome, biotin or a radioactive label may be used in such an amplification reaction. The label may be conjugated to one or both of the primers. Alternatively, the pool of nucleotides used in the amplification is labeled, so as to incorporate the label into the amplification product.

The sample nucleic acid, e.g. amplified or cloned may be analysed using any suitable method known in the art. For example, the nucleic acid may be sequenced by dideoxy or other methods, and the sequence of bases compared to the deleted sequence. Hybridization with the variant sequence may also be used to determine its presence, by Southern blots, dot blots, etc. The hybridization pattern of a control and variant sequence to an array of oligonucleotide probes immobilized on a solid support, as described in WO95/35505, may be used as a means of detecting the presence or absence of a sequence.

In one embodiment, the kit contains an antigen preparation prepared as described above and then fixed onto a solid support for use in a serological assay. The kit may also contain an explanatory note on how to proceed.

The kit can then be used to perform the methods of this invention described above.

Vaccines

As described above, the present invention also extends to vaccines for use in protecting against tuberculosis and tuberculosis-associated diseases.

One way of making a vaccine according of or for use in the invention is by biochemical purification of the immunogenic polypeptides from bacteria.

Alternatively, expression products of the genes encoding the polypeptides according to the invention may be used in vaccines. Such vaccines based upon the expression products of these genes can easily be made by admixing one or more proteins with a pharmaceutically acceptable carrier.

Alternatively, a vaccine according to the invention can comprise live recombinant carriers, capable of expressing the polypeptides according to the invention.

Vaccines described above all contribute to active vaccination, i.e. the host's immune system is triggered by one or more proteins according to the invention or immunogenic fragments thereof, to make antibodies against these proteins.

Alternatively, such antibodies can be raised in e.g. rabbits or can be obtained from antibody-producing cell lines. Such antibodies can then be administered to the host animal. This method of vaccination, passive vaccination, is the vaccination of choice when an animal is already infected, and there is no time to allow the natural immune response to be triggered. It is also the preferred method for vaccinating immune-compromised animals.

Therefore, one other form of this embodiment of the invention relates to vaccines comprising antibodies against one or more of the immunogenic polypeptides used in the invention.

An alternative and efficient way of vaccination is direct vaccination with DNA encoding the relevant antigen. Direct vaccination with DNA encoding proteins has been successful for many different proteins. (As reviewed in e.g. Donnelly et al. The Immunologist 2:20-26 (1993)). Therefore, still other forms of this embodiment of the invention relate to vaccines comprising nucleic acid sequences encoding a polypeptide as used in the invention or immunogenic fragments thereof, and to vaccines comprising DNA fragments that comprise such nucleic acid sequences.

Still other forms of this embodiment relate to vaccines comprising recombinant DNA molecules according to the invention.

DNA vaccines can easily be administered through intradermal application e.g. using a needle-less injector.

Vaccines according to the present invention may comprise a pharmaceutically acceptable carrier e.g. sterile water, a sterile physiological salt solution, or a buffer, and may also contain an adjuvant.

The invention will now be described further in the following non-limiting examples. Reference is made to the accompanying drawings in which:

FIG. 1 shows a Venn diagram illustrating the expression of antigens between different *Mycobacterium* strains; Group 1 (strain differentiation)-Rv1573, Rv1580c, Rv1585c, Rv1572c, MAP4244, MAP3779, MAP1522, MAP1607c); Group 2 (Early antigen)-Rv3614c, Rv3616c, ESAT6, CFP10, Rv2846c, alpha-crystallin 2; Group 3 (covering complete life cycle)-MCE1a, MCe4a, Rv2224c, Rv0283, RPFc.

FIG. 5 illustrates Commassie Blue stain showing purified mycobacterial proteins/fragments;

Figure 2A:
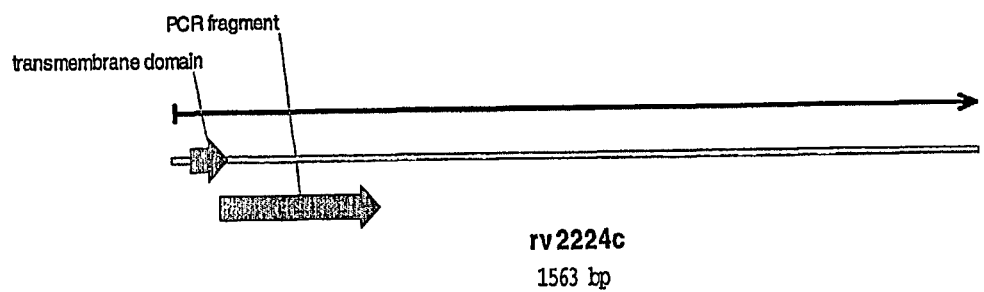
FIG. 2a is a schematic representation of rv2224c fragment which was amplified from *M. tuberculosis* genomic DNA.

FIG. 6 illustrates Western blots showing specific detection of mycobacterial proteins by rabbit polyclonal antibodies. Rabbit models were immunised with purified mycobacterial recombinant protein. In each case the rabbit host produced a strong specific immune response;

FIG. 7 illustrates ELISA screen of *M. bovis* target proteins using rabbit serum from animals immunised with Avian PPD. Serum was tested for presence of target specific IgM;

FIG. 8 illustrates ELISA screen of *M. bovis* target proteins using rabbit serum from animals immunised with Avian PPD. Serum was tested for presence of target specific IgG;

FIG. 9 illustrates ELISA screen of *M. bovis* target proteins using rabbit serum from animals immunised with Bovis PPD. Serum was tested for presence of target specific IgM;

FIG. 10 illustrates ELISA screen of *M. bovis* target proteins using rabbit serum from animals immunised with Avian PPD. Serum was tested for presence of target specific IgG;

FIG. 11 illustrates Cell Mediated Immunity Assay displaying results obtained when *M. bovis* proteins/fragments were tested against TB negative pre-infection bovine samples;

FIG. 12 illustrates the results of a Cell Mediated Immunity Assay indicating the ability of *M. bovis* proteins to detect infection in bovine samples;

FIG. 13 illustrates a western blot showing detection of early *M. bovis* TB Infection in bovine samples (Sample tested positive for antibody to response to Alpha crystallin 2, Rv1573 and Rv1580c);

FIG. 14 illustrates a western blot showing detection of late *M. bovis* TB Infection in bovine samples (Sample tested positive for antibody to response to Rv1573);

FIG. 15 illustrates the results of western blots demonstrating the humoral immune response of *M. bovis* TB infection in bovine samples (samples were analysed for bovine IgM and IgG antibodies).

EXAMPLES

The inventors have used bioinformatics software to identify and characterise proteins which are specific to one or other mycobacterial strains. Using a genome alignment strategy the group has identified point mutations or deletions which allow differentiation between *M bovis*, PPD (*M. bovis* AN5 and *M. avium*), *M. bovis* BCG and environmental mycobacteria. By concentrating on the various immunogenic regions which are deleted in specific strains, they have identified a panel of proteins capable of strain identification (Table 1). The inventors have surprisingly found that many of their selected proteins and protein fragments have been expressed in a soluble form. This soluble nature is indicative of correct conformation of the protein antigens therefore both linear and conformational epitopes are available for stimulation and detection purposes.

Methodology

Cloning, Expression and Purification of Mycobacterial Antigens:

DNA encoding target mycobacterial antigens (Table 2a, 2b, 2c and 2d) were identified and analysed by bioinformatics software. Primers were designed to amplify selected antigenic fragments of each of the target antigen by PCR by standard approaches. The PCR mixture contained 10 ng *M.*

*tuberculosis* genomic DNA as template in a total volume of 50 µl with 47 µl Taq polymerase supermix (1 Unit of recombinant enzyme), and 1 µl of each primer (10 pMol). The amplification was carried out with initial heating at 95° C. for 4 min followed by 25 cycles of denaturation at 95° C. for 30 s, annealing at 55° C. for 30 s, and extension at 72° C. for 1 min in each cycle. The final polymerisation was carried out for 10 min. The PCR products were analysed by 1.5% agarose gel electrophoresis, and purified. Each PCR product after purification was digested with appropriate enzymes and cloned in a pQE30 vector. (Any other suitable bacterial expression vector could be use, for example any vector incorporating an N terminal (his)$_6$ tag, such as a pQE or pET series vector) The resultant constructs were characterised by sequencing using Big dye terminator chemistry and automated DNA sequencer (ABI Prism 3100).

Recombinant mycobacterial antigens were expressed using standard conditions. Competent TOP10F' *E-coli* cells were transformed with various recombinant plasmids. The successful transformed cells were picked and grown into 5 ml LB containing 100 µg/ml of ampicillin at 37° C. with shaking overnight. 100 µl of this culture was used to inoculate a 500 ml of pre-warmed medium with antibiotics listed above and cultured at 37° C. for 120 min at 300 rpm. Expression of recombinant antigen was induced from the cells at this time with 1 µl/ml of 25 mM IPTG, and the cells cultured for a further 4 hours. The induced recombinant protein was lysed in 50 mls of 8 M urea buffer (480 g Urea, 29 g NaCl, 3.12 g NaH2PO4 (dihydrate), 0.34 g Imidazole) overnight. The solution was centrifuged at 6000 rpm for 1 hr, after which the supernatant was filtered using 0.8 µm gyrodisc filters before purification. The protein was purified by its N-terminal hexa-histidine tag and refolded using on-column refolding by immobilized metal affinity chromatography. This methodology allows for the purification of proteins from *E. coli* with little or no endotoxin contamination. Chelating hi-trap columns (Amersham Biosciences) were charged using 100 mM nickel sulphate before attachment to the Aktaprime chromatography system. Refolding takes place by the exchange of the 8 M urea buffer with a 5 mM imidazole wash buffer (29 g NaCl, 3.12 g NaH2PO4 (dihydrate) 0.34 g Imidazole, pH 8.0) and elution of the protein using a 500 mM imidazole elution buffer (29 g NaCl, 3.12 g NaH2PO4 (dihydrate), 34 g Imidazole).

The eluted fractions were subjected to SDS-PAGE analysis to confirm recombinant protein presence in eluted fractions. The gels were stained with coomassie blue overnight and subsequently destained to determine the fractions containing the recombinant antigens.

Antigen Immunisation and Test Bleeds:

Purified recombinant mycobacterial antigens concentration was estimated by comparison against know standards of BSA on Coomassie stained SDS-PAGE gel. New Zealand White rabbits were immunized with 100 µg of each recombinant antigen. On day 21 after the 1$^{st}$ immunization, the animals were given their second boost and they received their third boost on day 42. Test bleeds were taken 1 week post alternate immunisation boosts. The bleeds were allowed to clot overnight at 4° C., then centrifuged at 3000 rpm for 10 min, and the supernatant was aspirated. The collected serum was tested against each specific recombinant antigen by E.C.L. or Western Blot assays using standard methods. A 10 µg/ml aliquot of antigen was separated by SDS-PAGE and transferred onto Hybond-C Extra nitrocellulose membrane (Amersham Biosciences). The membrane was blocked by incubation in PBS/3% marvel for 1 hr at room temperature, after which it was rinsed briefly in PBS. The rabbit serum samples were used at a 1:500 and 1:1000 dilution in PBS and incubated on the membrane overnight at 4° C. while gently rocking. The blot was then rinsed three times with PBS/1% marvel and 0.1% Tween-20 and then incubated with the anti-rabbit HRP conjugated secondary antibody at a 1:5000 dilution for 1 hr at room temperature while shaking. The blot was then rinsed three times with the PBS/1% marvel and 0.1% Tween-20 solution, followed by a short rinse in PBS. The blot was incubated with ECL plus substrate (Amersham Biosciences) for 5 mins at room temperature before development using Kodak photographic film under safe light conditions.

PPD Studies:

New Zealand White rabbits were immunized with 100 µg PPD *M. bovis* AN5 or PPD *M. avium*. On day 21 after immunization, the animals were given their second boost and they received their third boost on day 42. Test bleeds were taken every week after 1st immunisation. The bleeds were allowed to clot overnight at 4° C., then centrifuged at 3000 rpm for 10 min, and the supernatant was aspirated. The collected serum was tested with our panel of recombinant mycobacterial antigens by ELISA and immunoblot systems using standard methods. Maxi Sorb 96 well plates were coated with recombinant antigen by adding 100 μl of coating buffer (Buffer A: 0.42 g sodium bicarbonate/100 μl $H_2O$, Buffer B: 0.53 g sodium carbonate/100 μl $H_2O$, pH 9.5) containing the screening antigen to each well (100 ng/well). A control antigen was also used to eliminate non-specific clones. The plates were incubated at 37° C. for 1 hr to allow the antigen to bind to the well and then blocked for 1 hr at room temperature by adding 200 μl PBS/3% BSA to each well. The blocking solution was removed from the plates and 100 μl of test serum was added to all antigen wells. The screening plates were incubated with supernatant for 1 hr on a rocker at room temperature. The plates were washed three times with PBS-T, after which 100 μl of anti-rabbit HRP conjugated secondary antibody (1:5000)(IgG & IgM) was added to each well and incubated for 1 hr at room temperature. The plates were washed three times with PBS-T and 100 μl of 3,3',5,5'-tetramethylbenzidine (TMB) was added to each well and incubated for 5 mins at 37° C. Positive wells were indicated by a colour development and the reaction was stopped by addition of 50 μl 1 M HCL. Plates were read by a spectrophotometer at 450 nm.

CMI Assay

Samples were obtained from an experimental bovine herd (both pre and post infection) housed in a controlled environment. Animals of approximately 6 months old with a TB free herd status were infected with *M. bovis* using standard methods (aerosol challenge). Whole blood samples were obtained prior to infection and 11 weeks after infection. Whole blood cultures were set up in 96 well plates and stimulated with antigen/protein fragment/PPD at 37° C. in 5% $CO_2$ for 24 hours. After the incubation period plasma supernatants were harvested and IFN gamma was determined by ELISA using standard methods. The results are presented using an optical density index (ODI=test antigen OD/PBS control OD).

Western blotting of TB positive samples. Serum samples obtained from skin test positive cattle were tested against a range of mycobacterial antigens using standard western blotting methods. Samples were tested for the presence of an IgM and IgG *M. bovis* specific antibodies to differentiate early infection from late infection. A 10 μg/ml aliquot of protein/antigen was separated by SDS-PAGE and transferred onto Hybond-C Extra nitrocellulose membrane (Amersham Biosciences). The membrane was blocked by incubation in PBS/3% marvel for 1 hr at room temperature, after which it was rinsed briefly in PBS. The bovine serum were used at a 1:500 dilution in PBS and incubated on the membrane overnight at 4° C. while gently rocking. The blot was then rinsed three times with PBS/1% marvel and 0.1% Tween-20 and then incubated with the rabbit anti-bovis HRP (IgM, IgA & IgG) conjugated secondary antibody at a 1:3000 dilution for 1 hr at room temperature while shaking. The blot was then rinsed three times with the PBS/1% marvel and 0.1% Tween-20 solution, followed by a short rinse in PBS. The blot was incubated with ECL plus substrate (Amersham Biosciences) for 5 mins at room temperature before development using Kodak photographic film under safe light conditions Results Expression and Purification of Proteins Transformed cells harbouring the correct constructs for target proteins (Table 1) were selected by colony pcr and sequencing. Expressed target proteins were identified by SDS PAGE analysis of cell lysates (Data not shown). Each target protein was successfully purified by IMAC following IPTG induced expression. Protein purity was confirmed using Commassie blue gels.

Figure 2B:
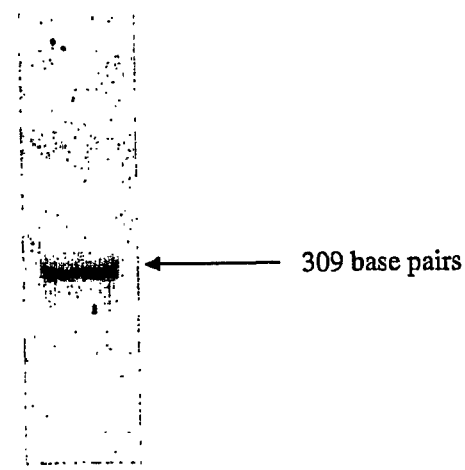
FIG. 2b shows a PCR product.
Figure 3:
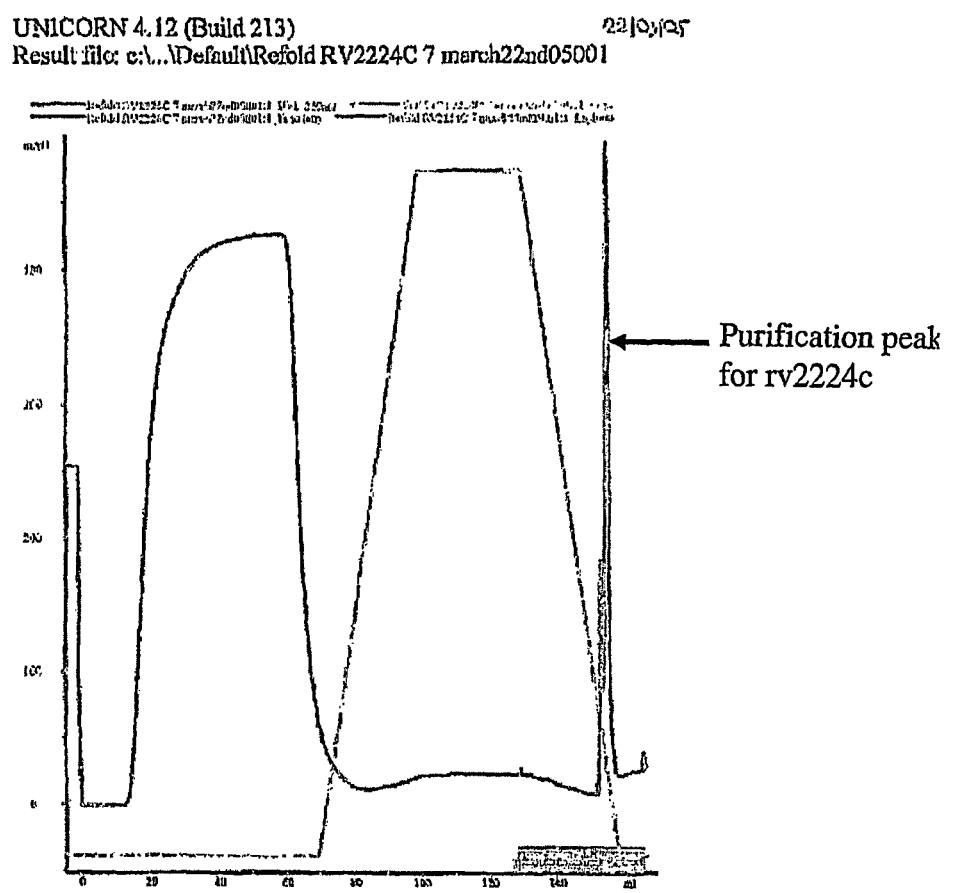
FIG. 3 illustrates an elution profile of the rv2224c fragment.
Figure 4:
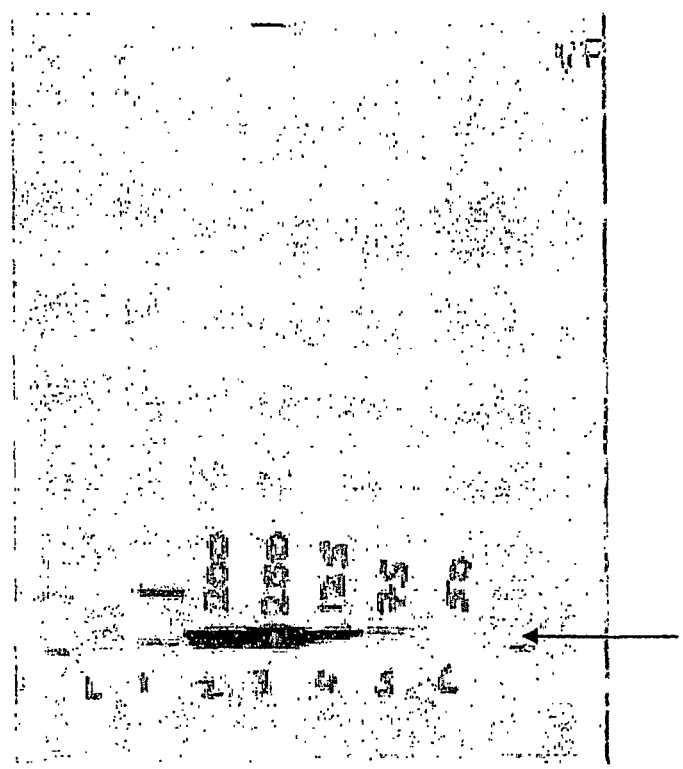
FIG. 4 illustrates a Western blot of eluted fractions stained with Coomassie Blue.

The following example relates to the preparation of the Rv2224c fragment corresponding to SEQ ID NO: 13. A rv2224c fragment was amplified from *M. tuberculosis* genomic DNA in a 50 µl reaction (FIG. 2*a*). A 309 bp product was obtained (FIG. 2*b*). The PCR product was restricted with BamHI and Xho1 and cloned into an expression vector. Successful cloning was confirmed by PCR and sequencing. The Rv2224c fragment was expressed in 250 ml flasks LB, with induction with IPTG at an OD600~0.6. The tagged peptide was purified with the elution trace shown in FIG. 3. A strong elution peak was obtained. The eluted fractions were analysed for protein purity and quantity. FIG. 5 shows a Western blot of the protein fractions obtained at the peak of the elution profile (lanes 2-6). The concentrations indicated next to each lane are in $\mu g \mu l^{-1}$.

Antibody Production

Target specific antibodies were produced for each of the selected proteins Each recombinant protein was capable of inducing a strong immune response in the absence of any adjuvant demonstrating that these target proteins will induce an immune response in *M. bovis* challenged animals. The antibodies showed no cross reactivity with other mycobacterial proteins by western blot at a 1:500 dilution (FIG. 6).

Analysis of PPD

The inventors have examined the serological specificity of these recombinant protein antigens by testing sera from experimental in vivo models (Rabbits) challenged with PPD avian and PPD bovis to evaluate the diagnostic potential in a range of situations using immunoblotting and ELISA systems. Test bleeds from rabbits immunised with 100 ug of Avian PPD or Bovine PPD were taken weekly and tested against a panel of target antigens by ELISA to examine any immune response. Serum from neither the Avian PPD nor Bovine PPD challenged hosts induced a strong immune response to any of the target proteins when tested by either IgM or IgG secondary antibodies (FIGS. 7-10). A number of the selected antigens are not present in the mycobacterial strains used for production of PPD, while those present may be inactivated or non-immunogenic when delivered in PPD format. It is possible that the harsh production conditions used for PPD causes damage to conformational epitopes which may be strongly immunogenic. This finding is important in two ways.

Firstly, it suggests that an *M. Bovis* infected animal that is tested with PPD skin test may not elicit a response to certain mycobacterial proteins (antigenic epitopes) even though bovis specific antigens/fragments are present. This would lead to false negative results with conventional testing by both the skin test method and CMI method. This type of false negative analysis would most likely occur with low bacterial load present.

Secondly, the fact that these proteins do not elicit a response with the PPD reagents suggests that they could be successfully used on animals previously challenged with PPD without false positive results. The likelihood of obtaining false positive results are further reduced by using a 'multiple protein panel' whose patterns of positivity allow accurate strain specific diagnosis. These panels of antigens discriminate between these various forms of immune reaction and enables discrimination between animals that have been inoculated with PPD, challenged with environmental strains, been vaccinated or animals that have been truly infected by wild-type TB. Additionally these antigens allow discrimination of early infection and discrimination between early and late infection.

Analysis of Cell Mediated Immune Response

The selected panel of recombinant proteins were tested for their ability to induce an immune response in cells taken from experimentally infected animals. A CMI assay, the present gold standard, was carried out on cells both pre-infection and 11 weeks post-infection with *M. bovis* (FIGS. 11-12). PPD Avian and PPD Bovis were used as controls. An ODI of >/=2 is considered positive. Most antigens gave no response when used in the pre-infection assay. Three antigens, namely Rv2224c, Rv3614c and RPF all gave a false positive response. This may indicate their unsuitability for CMI type assays. With respect to 3614c, the inventors believe that, although this antigen is occasionally found in some strains of tuberculosis other than bovine, the confirmation of its presence or the presence of an immune response to it is nevertheless most likely to indicate the presence of a bovine strain of *Maycobacterium* or an immune response thereto.

When all the other proteins were analysed, for their ability to detect an interferon response, all proteins displayed good diagnostic potential. It should be noted that the PPD Avian gave a false positive result for one of the infected animals. This is a major problem with the use of such a crude reagent. The use of CFP10 along with PPD in CMI assays has previously been performed and has improved sensitivity. It is however important to state that due to the heterogeneous nature of the disease it is necessary to use multiple proteins/fragments to obtain full coverage of the disease population. The results obtained for Rv3616c show the ability to detect positive disease in 80% of samples tested when used alone. The combination of Rv3616c with Rv3870, Rv0283 fragments and CFP10 offer a very definitive assay on tests performed on animals with a known infective strain. In addition, the identification of other strongly immunogenic antigens such as one or more of Rv1573, Rv1580c, Rv1585c and Rv1572c allows definitive identification of infection with *M bovis*.

Analysis of TB infected serum by Western blot. Serum samples from skin test positive cattle were tested for antigen recognition using a panel of mycobacterial antigens (FIGS. 13 & 14). FIG. 13 shows the antigen recognition profile for a known skin test positive sample. The serum shows a positive specific response for Alpha crystalline 2, Rv1573 and Rv1580c. The response is observed against the Anti-bovis IgM antibody only. This indicates an early infection. FIG. 14 shows the antigen recognition profile for a known skin test positive sample. The serum shows a positive specific response for Rv1573. This response is observed against the anti-bovis IgG antibody only. This indicates that the infection is at a more advanced/later stage. FIG. 15 shows detection of a humoral immune response to the other *M. bovis* proteins/fragments when tested using skin test positive cattle samples.

In certain instances the response is an early IgM response while in others it is a later IgG response. The results show that it is necessary use multiple proteins/fragments to obtain full coverage of the disease population.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

TABLE 1

Target antigens

| Antigen | RD Region | Antigenic | Early antigen | Strain differentiation | | | |
|---|---|---|---|---|---|---|---|
| | | | | M. bovis wild type | M. bovis AN5 (PPD) | M. avium (PPD) | M. microti |
| Rv3616c (Mtb40) | – | Yes | Yes | + | + | – | – |
| Rv0251c (α-crystallin 2) | – | Yes | Yes | + | + | – | – |
| Rv3875 (ESAT6) | 1 | Yes | Yes | + | + | – | – |
| Rv3874 (CFP10) | 1 | Yes | Yes | + | + | – | – |
| Rv1572c | 3 | Yes | – | – | + | – | + | 
| Rv1573 | 3 | Yes | – | – | + | – | + |
| Rv1580c | 3 | Yes | – | – | + | – | – |
| Rv1585c | 3 | Yes | – | – | + | – | – |
| Rv3870 | 1 | Yes | – | – | + | + | – |
| Rv2224c | – | | – | – | + | + | + |
| Rv0283 | – | | – | – | + | + | + |
| Rv1884c (RPFc) | – | Yes | – | – | + | + | + |
| Rv0169 (MCE1a) | – | Yes | – | – | + | + | + |
| Rv3499c (MCE4a) | – | Yes | – | – | + | + | + |

TABLE 2a

Early antigens for wild-type TB infection

| Antigen | Sequences |
|---|---|
| Rv3616c (Mtb40) | Fragment 304-392 amino acids ASTRQALRPRADGPVGAAAEQVGGQSQLVSAQGS QGMGGPVGMGGMHPSSGASKGTTTKKYSEGAAAG TED (SEQ ID NO: 1) |
| Rv0251c (α-crystallin 2) | Full length MNNLALWSRPVWDVEPWDRWLRDFFGPAATTDWY RPVAGDFTPAAEIVKDGDDAVVRLELPGIDVDKN VELDPGQPVSRLVIRGEHRDEHTQDAGDKDGRTL REIRYGSFRRSFRLPAHVTSEAIAASYDAGVLTV RVAGAYKAPAETQAQRIAITK (SEQ ID NO: 12) |
| Rv3875 (ESAT6) | Full length TEQQWNFAGIEAAASAIQGNVTSIHSLLDEGKQS LTKLAAAWGGSGSEAYQGVQQKWDATATELNNAL QNLARTISEAGQAMASTEGNVTGMFA (SEQ ID NO: 7) |

TABLE 2a-continued

Early antigens for wild-type TB infection

| Antigen | Sequences |
|---|---|
| Rv3874 (CFP10) | Full length AEMKTDAATLAQEAGNFERISGDLKTQIDQVEST AGSLQGQWRGAAGTAAQAAVVRFQEAANKQKQEL DEISTNIRQAGVQYSRADEEQQQALSSQMGF (SEQ ID NO: 8) |

TABLE 2b

Antigens in RD 3 region reported absent in bovine PPD (M. bovis AN5) and M. bovis BCG

| Antigen | Sequence |
|---|---|
| Rv1572c | Full length MECSSAVHGQPRTNTFHHHEKLLRHNDEDNHDDP (SEQ ID NO: 5) |
| Rv1573 | Full length MTTTPARFNHLVTVTDLETGDRAVCDRDQVAETIRAWFPDAP LEVREALVRLQAALNRHEHTGELEAFLRISVEHADAAGGDEC GPAILAGRSGPEQAAINRQLGLAGDDEPDGDDTPPWSRMIGL GGGSPAEDER (SEQ ID NO: 2) |
| Rv1580c | Full length MAETPDHAELRRRIADMAFNADVGMATCKRCGDAVPYIILPN LQTGEPVMGVADNKWKRANCPVDVGKPCPFLIAEGVADSTDD TIEVDQ (SEQ ID NO: 3) |

TABLE 2b-continued

| Antigens in RD 3 region reported absent in bovine PPD (*M. bovis* AN5) and *M. bovis* BCG | |
|---|---|
| Antigen | Sequence |
| Rv1585c | Full length<br>MSRHHNIVIVCDHGRKGDGRIEHERCDLVAPIIWVDETQGWL<br>PQAPAVATLLDDDNQPRAVIGLPPNESRLRPEMRRDGWVRLH<br>WEFACLRYGAAGVRTCEQRPVRVRNGDLQTLCENVPRLLTGL<br>AGNPDYAPGFAVQSDAVVVAMWLWRTLCESDTPNKLRATPTR<br>GSC<br>(SEQ ID NO: 4) |

TABLE 2c

| Antigens for wild-type TB infection | |
|---|---|
| Antigen | Sequence |
| Rv3870 | 84-192 amino acids<br>GLAGSTGGGGKKVPEINADRKEYLRYLAGLRTRVTSSATSQV<br>AFFSYHAPHPEDLLSIVGTQRQWSRPANADFYAATRIGIGDQ<br>PAVDRLLKPAVGGELAAASAAPQPF<br>(SEQ ID NO: 6) |
| Rv2224c | 32-137 amino acids<br>CIRVVGGRARMAEPKLGQPVEWTPCRSSNPQVKIPGGALCGK<br>LAVPVDYDRPDGDVAALALIRFPATGDKIGSLVINPGGPGES<br>GIEAALGVFQTLPKRVHER<br>(SEQ ID NO: 13) |
| Rv0283 | Fragment 1: 1-53 amino acids<br>MTNQQHDHDFDHDRRSFASRTPVNNNPDKVVYRRGFVTRHQV<br>TGWRFVMRRIA<br>(SEQ ID NO: 9)<br>Fragment 2: 120-196 amino acids<br>EQLHPVLNLTSARLIVGRPVSPTTVKSTELDQFPRGNLIGIP<br>GAPERMVQNTSTDANWTVCDGLNAPSRGGADGVG<br>(SEQ ID NO: 10)<br>Fragment 3: 319-393 amino acids<br>QYYAVLPDGLQQISPVLAAILRNNNSYGLQQPPRLGADEVAK<br>LPVSRVLDTRRYPSEPVSLVDVTRDPVTCAYWSKP<br>(SEQ ID NO: 11) |
| RPFc | Fragment 1: 72-111 amino acids<br>WDAVAQCESGGNWAANTGNGKYGGLQFKPATWAAFGGVG<br>(SEQ ID NO: 16)<br>Fragment 2: 72-138 amino acids<br>WDAVAQCESGGNWAANTGNGKYGGLQFKPATWAAFGGVGNPA<br>AASREQQIAVANRVLAEQGLDAWP<br>(SEQ ID NO: 17) |
| MCE1a | 322-380 amino acids<br>TNSEILSGIGISLLSPLALATNGAAIGIGLVAGLIAPPLAVA<br>ANLAGALPGIVGGAPNPYTYPEN<br>(SEQ ID NO: 14) |
| MCE4a | 270-400 amino acids<br>NRLRAPLKVTSDYSPVFGCLFKGIARGVKEFAPLIGVRKAGL<br>FTSSSFVLGAPSYTYPESLPIVNASGGPNCRGLPDIPTKQTG<br>GSFYRAPFLVTDNALIPYQPFTELQVDAPSTLQFLFNGAFAE<br>RDDF<br>(SEQ ID NO: 15) |

TABLE 2d

| Antigen | Sequence |
|---|---|
| MAP4244 (avium ESAT6 | Full length<br>MDPTLSYNFGEIEHSVRQEIHTTSARFNAALDELFARIAPLQ<br>QLWTSEAATAYQAEQLKWHRSATALNEILVQLGDAVRDGAEE<br>VADADRRAAGVWAR<br>(SEQ ID NO: 19) |
| MAP3779 (avium Rv0283) | 179-223 amino acids<br>AVSEPGGHAAHSAGVTVIAGRPDSSGARAATLPSRQALLADR<br>DGT<br>(SEQ ID NO: 20) |
| MAP1522 | 181-287 amino acids<br>AQAAALGEATGRGAGTVAADATAPPSGIISQLLEALGNASRG<br>YMDFWDQVLNTLTGSPLAGTTWQNTFGILADIGRFSTVANDS<br>MSPINLAMTEFKMFYKLPVEGLD<br>(SEQ ID NO: 21) |
| MAP1607c (avium RPFc) | Full length<br>MFSPAEMAVFADRRHISRHF RIGNALATRA EILDMTNLCK<br>LLVKSVVVGGFVAASMASSTGVVSAEPTPNWDAIAQCESGGN<br>WHANTGNGEYGGLQFKPATWARYGGVGNPAAASREQQIAVAN<br>RVFAEEGVEPWPKCGAQSGLPIGWYSHPAQGIKQIINGLIQA<br>AVPR<br>(SEQ ID NO: 22) |

REFERENCES

L. M. O'Reilly and C. J. Daborn, *Tub. Lung Dis.* 761 (1995), pp. 1-46.

J. P. Caffrey, *Vet. Microbiol.* 40 (1994), pp. 1-4.

M. L. Monaghan et al, *Vet. Microbiol.* 40 (1994), pp. 111-124.

P. R. Wood et al, *Vet. Microbiol.* 31 (1992), pp. 71-79.

Cockle et al. (2002) Infection and Immunity p. 6996-7003

Alexander et al. (2003) *Nature Medicine* 9, 533-539

Pym et al. (2003) Nature Publishing Group p. 533-539

Gioffre A et al. (2005) Microbes Infect. March; 7(3): 325-334

Behr M. A. et al. (1999) Science May; 28: 1520-1523

R. Al-Attiyah et al. (2004) *Clin Exp Immunol* 138: 139-144

Andersen P. and Doherty T. M. (2005) *Microbes and Infection* (In press)

McNair J et al. (2001) *Scand. J. Immunol.* 53:365-371

Lightbody et al. (1998) *Vet. Rec.* 142: 295-300

Lightbody et al. (2000) *Vet. Microbiol.* 75: 177-188

Mattow J. et al. (2001) *Electrophoresis* 22: 2936-2946

Gordon S. V. et al. (1999) *Molecular Microbiology* 32(3): 643-655

Inwald J. et al. (2003) *Journal of Clinical Microbiology* 41:3929-3932

Mahairas, G. G. et al. (1996) *American Society for Microbiology* 178:1274-1282

Kitamura et al. (1998) *Nippon Rinsho* 56(12): 3036-40

Brodin et al. (2002) *American Society for Microbiology* October: 5568-5578

Garcia-Pelayo et al. (2004) *Tuberculosis* 84: 159-166

The invention claimed is:

1. A diagnostic kit for the diagnosis of the presence of tuberculosis in a biological sample, said kit comprising:
   (i) the polypeptide having the amino acid sequence shown as SEQ ID NO:5; and
   (ii) the polypeptide having the amino acid sequence shown as SEQ ID NO:1; and
   (iii) the polypeptide having the amino acid sequence shown as SEQ ID NO:7; and
   (iv) optionally at least one polypeptide selected from the polypeptides having the amino acid sequence shown as any one of SEQ ID NO:2, SEQ ID NO:3, and SEQ ID NO:4; and
   (v) optionally, at least one polypeptide selected from the polypeptides having the amino acid sequence shown as any one of SEQ ID NO:6, SEQ ID NO:8 or SEQ ID NO:23.

2. A diagnostic kit for the diagnosis of the presence of tuberculosis in a biological sample, wherein the kit comprises:
   a polypeptide having the amino acid sequence shown as SEQ ID NO:5; and
   (ii) at least one of the polypeptides having the amino acid sequence shown as SEQ ID NOS: 1, 6, 7, 8 and 23; and
   (iii) optionally at least one of the polypeptides having the amino acid sequence shown as SEQ ID NO: 2, 3 or 4.

3. A diagnostic it for the diagnosis of the presence of tuberculosis in a biological sample, said kit comprising:
   (i) the polypeptide having the amino acid sequence shown as SEQ ID NO:5; and
   (ii) one or more polypeptides selected from the polypeptides having the amino acid sequence shown as any one of SEQ ID NO:1, SEQ ID NO:2, SEQ ID NO:3, SEQ ID NO:4, SEQ ID NO: 6, SEQ ID NO:7, SEQ ID NO:8, or SEQ ID NO: 23.

4. The kit according to claim 3, wherein the kit comprises a polypeptide having the amino acid sequence shown as SEQ ID NO: 1.

5. The kit according to claim 3, wherein the kit comprises at least one polypeptide having the amino acid sequence shown as SEQ ID NO: 2, 3 or 4.

6. The kit according to claim 3 wherein the kit comprises:
   (i) at least one of the polypeptides having the amino acid sequence shown as SEQ ID NO: 1, 6, 7, 8 or 23; and
   (ii) optionally at least one of the polypeptides having the amino acid sequence shown as SEQ ID NO: 2, 3 or 4.

7. A method of detecting exposure to *Mycobacterium* in an animal or in a biological sample from said animal, the method comprising the step of detecting the presence or absence of an immune response to:
   (i) the polypeptide having the amino acid sequence shown as SEQ ID NO:5; and
   (ii) the polypeptide having the amino acid sequence shown as SEQ ID NO:1; and
   (iii) the polypeptide having the amino acid sequence shown as SEQ ID NO:7; and
   (iv) optionally at least one polypeptide selected from the polypeptides having the amino acid sequence shown as any one of SEQ ID NO:2, SEQ ID NO:3, and SEQ ID NO:4; and
   (v) optionally at least one polypeptide selected from the polypeptides having the amino acid sequence shown as any one of SEQ ID NO:6, SEQ ID NO:8 or SEQ ID NO:23;
   wherein the presence of an immune response to one or more of said polypeptides is indicative of the exposure of the animal to *Mycobacterium*.

8. The method according to claim 7, wherein the *Mycobacterium* is *Mycobacterium bovis*.

9. The method according to claim 7, wherein the detection of the presence of (i) an immune response to at least one of the polypeptides having the amino acid sequence shown as any one of SEQ ID NO:2, SEQ ID NO:3, SEQ ID NO:4, and SEQ ID NO:5 and (ii) an immune response to at least one of the polypeptides having the amino acid sequence shown as any one of SEQ ID NO:1, SEQ ID NO:6, SEQ ID NO:7, SEQ ID NO:8 or SEQ ID NO:23, is indicative of the presence of tuberculosis infection in the animal.

10. The method according to claim 7, wherein the presence of an immune response to a polypeptide having the amino acid sequence shown as SEQ ID NO: 1 is detected.

11. The method according to claim 7, wherein the presence of an immune response to a polypeptide having the amino acid sequence shown as SEQ ID NO: 5 is detected.

12. The method according to claim 7, wherein the presence of:
   (i) an immune response to at least one of the polypeptides having the amino acid sequence shown as SEQ ID NOS: 2, 3, 4, or 5; and
   (ii) an immune response to at least two of the polypeptides having the amino acid sequence shown as SEQ ID NOS: 1, 6, 7, 8 or 23 is detected.

13. The method according to claim 7, wherein the detection of an immune response to each of:
   (i) the polypeptide having the amino acid sequence shown as SEQ ID NO:5; and
   (ii) the polypeptide having the amino acid sequence shown as SEQ ID NO:1; and
   (iii) the polypeptide having the amino acid sequence shown as SEQ ID NO:7; is indicative of the presence of bovine tuberculosis.

14. The method according to claim 7, further comprising the step of detecting the presence of one or more polypeptides having the amino acid sequence shown as SEQ ID NOS: 1, 2, 3, 4, 5, 6, 7, 8 or 23 by detecting the presence of an antibody response to said polypeptides.

15. The method according to claim 7, further comprising the step of detecting the presence of at least one of the polypeptides having the amino acid sequence shown as SEQ ID NOS: 1, 2, 3, 4, 5, 6, 7, 8 or 23 by detecting the presence of a nucleic acid encoding said polypeptide or by determining the presence of a nucleic acid encoding an antibody to said polypeptide.

16. An assay method for the detection of the presence of *Mycobacterium* in an animal or a biological sample from said animal, said method comprising the steps:
   providing a biological sample from said animal; and detecting the presence or absence of an immune response to:
   (i) the polypeptide having the amino acid sequence shown as SEQ ID NO:5; and
   (ii) one or more polypeptides selected from the polypeptides having the amino acid sequence shown as any one of SEQ ID NO:1, SEQ ID NO:2, SEQ ID NO:3, SEQ ID NO:4, SEQ ID NO: 6, SEQ ID NO:7, SEQ ID NO: 8, or SEQ ID NO:23;
   in the biological sample;
   wherein the presence of an immune response to one or more of said polypeptides is indicative of the presence of *Mycobacterium* in the biological sample.

17. The method according to claim 16, wherein the detection of the presence of an immune response to:
   (i) the polypeptide having the amino acid sequence shown as SEQ ID NO:5; and
   (ii) one or more polypeptides selected from the polypeptides having the amino acid sequence shown as any one of SEQ ID NO:1, SEQ ID NO:2, SEQ ID NO:3, SEQ ID NO:4, SEQ ID NO: 6, SEQ ID NO:7, SEQ ID NO: 8, or SEQ ID NO:23, is indicative of the presence of tuberculosis infection in the animal.

18. The method according to claim 16, wherein the *Mycobacterium* is *Mycobacterium bovis*.

19. The method according to claim 16, further comprising the step of detecting one or more polypeptides having the amino acid sequence shown as SEQ ID NOS: 1, 2, 3, 4, 5, 6, 7, 8 or 23.

20. The method according to claim 16, further comprising the step of detecting the presence of at least one of the polypeptides having the amino acid sequence shown as SEQ ID NOS: 1, 2, 3, 4, 5, 6, 7, 8 or 23 by detecting the presence of a nucleic acid encoding said polypeptide or by determining the presence of a nucleic acid encoding an antibody to said polypeptide.

* * * * *

SEQUENCE LISTING

<160> NUMBER OF SEQ ID NOS: 23

<210> SEQ ID NO 1
<211> LENGTH: 71
<212> TYPE: PRT

<213> ORGANISM: Mycobacterium tuberculosis

<400> SEQUENCE: 1

```
Ala Ser Thr Arg Gln Ala Leu Arg Pro Arg Ala Asp Gly Pro Val Gly
1               5                   10                  15

Ala Ala Ala Glu Gln Val Gly Gly Gln Ser Gln Leu Val Ser Ala Gln
            20                  25                  30

Gly Ser Gln Gly Met Gly Gly Pro Val Gly Met Gly Gly Met His Pro
        35                  40                  45

Ser Ser Gly Ala Ser Lys Gly Thr Thr Thr Lys Lys Tyr Ser Glu Gly
    50                  55                  60

Ala Ala Ala Gly Thr Glu Asp
65                  70
```

<210> SEQ ID NO 2
<211> LENGTH: 136
<212> TYPE: PRT
<213> ORGANISM: Mycobacterium tuberculosis

<400> SEQUENCE: 2

```
Met Thr Thr Thr Pro Ala Arg Phe Asn His Leu Val Thr Val Thr Asp
1               5                   10                  15

Leu Glu Thr Gly Asp Arg Ala Val Cys Asp Arg Asp Gln Val Ala Glu
            20                  25                  30

Thr Ile Arg Ala Trp Phe Pro Asp Ala Pro Leu Glu Val Arg Glu Ala
        35                  40                  45

Leu Val Arg Leu Gln Ala Ala Leu Asn Arg His Glu His Thr Gly Glu
    50                  55                  60

Leu Glu Ala Phe Leu Arg Ile Ser Val Glu His Ala Asp Ala Ala Gly
65                  70                  75                  80

Gly Asp Glu Cys Gly Pro Ala Ile Leu Ala Gly Arg Ser Gly Pro Glu
                85                  90                  95

Gln Ala Ala Ile Asn Arg Gln Leu Gly Leu Ala Gly Asp Asp Glu Pro
            100                 105                 110

Asp Gly Asp Asp Thr Pro Pro Trp Ser Arg Met Ile Gly Leu Gly Gly
        115                 120                 125

Gly Ser Pro Ala Glu Asp Glu Arg
    130                 135
```

<210> SEQ ID NO 3
<211> LENGTH: 90
<212> TYPE: PRT
<213> ORGANISM: Mycobacterium tuberculosis

<400> SEQUENCE: 3

```
Met Ala Glu Thr Pro Asp His Ala Glu Leu Arg Arg Arg Ile Ala Asp
1               5                   10                  15

Met Ala Phe Asn Ala Asp Val Gly Met Ala Thr Cys Lys Arg Cys Gly
            20                  25                  30

Asp Ala Val Pro Tyr Ile Ile Leu Pro Asn Leu Gln Thr Gly Glu Pro
        35                  40                  45

Val Met Gly Val Ala Asp Asn Lys Trp Lys Arg Ala Asn Cys Pro Val
    50                  55                  60

Asp Val Gly Lys Pro Cys Pro Phe Leu Ile Ala Glu Gly Val Ala Asp
65                  70                  75                  80

Ser Thr Asp Asp Thr Ile Glu Val Asp Gln
                85                  90
```

```
<210> SEQ ID NO 4
<211> LENGTH: 171
<212> TYPE: PRT
<213> ORGANISM: Mycobacterium tuberculosis

<400> SEQUENCE: 4

Met Ser Arg His His Asn Ile Val Ile Val Cys Asp His Gly Arg Lys
1               5                   10                  15

Gly Asp Gly Arg Ile Glu His Glu Arg Cys Asp Leu Val Ala Pro Ile
            20                  25                  30

Ile Trp Val Asp Glu Thr Gln Gly Trp Leu Pro Gln Ala Pro Ala Val
        35                  40                  45

Ala Thr Leu Leu Asp Asp Asn Gln Pro Arg Ala Val Ile Gly Leu
    50                  55                  60

Pro Pro Asn Glu Ser Arg Leu Arg Pro Glu Met Arg Arg Asp Gly Trp
65                  70                  75                  80

Val Arg Leu His Trp Glu Phe Ala Cys Leu Arg Tyr Gly Ala Ala Gly
                85                  90                  95

Val Arg Thr Cys Glu Gln Arg Pro Val Arg Val Arg Asn Gly Asp Leu
            100                 105                 110

Gln Thr Leu Cys Glu Asn Val Pro Arg Leu Leu Thr Gly Leu Ala Gly
        115                 120                 125

Asn Pro Asp Tyr Ala Pro Gly Phe Ala Val Gln Ser Asp Ala Val Val
    130                 135                 140

Val Ala Met Trp Leu Trp Arg Thr Leu Cys Glu Ser Asp Thr Pro Asn
145                 150                 155                 160

Lys Leu Arg Ala Thr Pro Thr Arg Gly Ser Cys
                165                 170

<210> SEQ ID NO 5
<211> LENGTH: 34
<212> TYPE: PRT
<213> ORGANISM: Mycobacterium tuberculosis

<400> SEQUENCE: 5

Met Glu Cys Ser Ser Ala Val His Gly Gln Pro Arg Thr Asn Thr Phe
1               5                   10                  15

His His His Glu Lys Leu Leu Arg His Asn Asp Glu Asp Asn His Asp
            20                  25                  30

Asp Pro

<210> SEQ ID NO 6
<211> LENGTH: 109
<212> TYPE: PRT
<213> ORGANISM: Mycobacterium tuberculosis

<400> SEQUENCE: 6

Gly Leu Ala Gly Ser Thr Gly Gly Gly Lys Lys Val Pro Glu Ile
1               5                   10                  15

Asn Ala Asp Arg Lys Glu Tyr Leu Arg Tyr Leu Ala Gly Leu Arg Thr
            20                  25                  30

Arg Val Thr Ser Ser Ala Thr Ser Gln Val Ala Phe Phe Ser Tyr His
        35                  40                  45

Ala Pro His Pro Glu Asp Leu Leu Ser Ile Val Gly Thr Gln Arg Gln
    50                  55                  60

Trp Ser Arg Pro Ala Asn Ala Asp Phe Tyr Ala Ala Thr Arg Ile Gly
65                  70                  75                  80
```

```
Ile Gly Asp Gln Pro Ala Val Asp Arg Leu Leu Lys Pro Ala Val Gly
             85                  90                  95

Gly Glu Leu Ala Ala Ser Ala Ala Pro Gln Pro Phe
            100                 105

<210> SEQ ID NO 7
<211> LENGTH: 94
<212> TYPE: PRT
<213> ORGANISM: Mycobacterium tuberculosis

<400> SEQUENCE: 7

Thr Glu Gln Gln Trp Asn Phe Ala Gly Ile Glu Ala Ala Ala Ser Ala
1               5                   10                  15

Ile Gln Gly Asn Val Thr Ser Ile His Ser Leu Leu Asp Glu Gly Lys
                20                  25                  30

Gln Ser Leu Thr Lys Leu Ala Ala Ala Trp Gly Gly Ser Gly Ser Glu
            35                  40                  45

Ala Tyr Gln Gly Val Gln Gln Lys Trp Asp Ala Thr Ala Thr Glu Leu
        50                  55                  60

Asn Asn Ala Leu Gln Asn Leu Ala Arg Thr Ile Ser Glu Ala Gly Gln
65                  70                  75                  80

Ala Met Ala Ser Thr Glu Gly Asn Val Thr Gly Met Phe Ala
                85                  90

<210> SEQ ID NO 8
<211> LENGTH: 99
<212> TYPE: PRT
<213> ORGANISM: Mycobacterium tuberculosis

<400> SEQUENCE: 8

Ala Glu Met Lys Thr Asp Ala Ala Thr Leu Ala Gln Glu Ala Gly Asn
1               5                   10                  15

Phe Glu Arg Ile Ser Gly Asp Leu Lys Thr Gln Ile Asp Gln Val Glu
                20                  25                  30

Ser Thr Ala Gly Ser Leu Gln Gly Gln Trp Arg Gly Ala Ala Gly Thr
            35                  40                  45

Ala Ala Gln Ala Ala Val Val Arg Phe Gln Glu Ala Ala Asn Lys Gln
        50                  55                  60

Lys Gln Glu Leu Asp Glu Ile Ser Thr Asn Ile Arg Gln Ala Gly Val
65                  70                  75                  80

Gln Tyr Ser Arg Ala Asp Glu Glu Gln Gln Gln Ala Leu Ser Ser Gln
                85                  90                  95

Met Gly Phe

<210> SEQ ID NO 9
<211> LENGTH: 53
<212> TYPE: PRT
<213> ORGANISM: Mycobacterium tuberculosis

<400> SEQUENCE: 9

Met Thr Asn Gln Gln His Asp His Asp Phe Asp His Asp Arg Arg Ser
1               5                   10                  15

Phe Ala Ser Arg Thr Pro Val Asn Asn Asn Pro Asp Lys Val Val Tyr
                20                  25                  30

Arg Arg Gly Phe Val Thr Arg His Gln Val Thr Gly Trp Arg Phe Val
            35                  40                  45

Met Arg Arg Ile Ala
        50
```

-continued

<210> SEQ ID NO 10
<211> LENGTH: 76
<212> TYPE: PRT
<213> ORGANISM: Mycobacterium tuberculosis

<400> SEQUENCE: 10

Glu Gln Leu His Pro Val Leu Asn Leu Thr Ser Ala Arg Leu Ile Val
1               5                   10                  15

Gly Arg Pro Val Ser Pro Thr Thr Val Lys Ser Thr Glu Leu Asp Gln
            20                  25                  30

Phe Pro Arg Gly Asn Leu Ile Gly Ile Pro Gly Ala Pro Glu Arg Met
        35                  40                  45

Val Gln Asn Thr Ser Thr Asp Ala Asn Trp Thr Val Cys Asp Gly Leu
    50                  55                  60

Asn Ala Pro Ser Arg Gly Gly Ala Asp Gly Val Gly
65                  70                  75

<210> SEQ ID NO 11
<211> LENGTH: 77
<212> TYPE: PRT
<213> ORGANISM: Mycobacterium tuberculosis

<400> SEQUENCE: 11

Gln Tyr Tyr Ala Val Leu Pro Asp Gly Leu Gln Gln Ile Ser Pro Val
1               5                   10                  15

Leu Ala Ala Ile Leu Arg Asn Asn Ser Tyr Gly Leu Gln Gln Pro
            20                  25                  30

Pro Arg Leu Gly Ala Asp Glu Val Ala Lys Leu Pro Val Ser Arg Val
        35                  40                  45

Leu Asp Thr Arg Arg Tyr Pro Ser Glu Pro Val Ser Leu Val Asp Val
    50                  55                  60

Thr Arg Asp Pro Val Thr Cys Ala Tyr Trp Ser Lys Pro
65                  70                  75

<210> SEQ ID NO 12
<211> LENGTH: 157
<212> TYPE: PRT
<213> ORGANISM: Mycobacterium tuberculosis

<400> SEQUENCE: 12

Met Asn Asn Leu Ala Leu Trp Ser Arg Pro Val Trp Asp Val Glu Pro
1               5                   10                  15

Trp Asp Arg Trp Leu Arg Asp Phe Phe Gly Pro Ala Ala Thr Thr Asp
            20                  25                  30

Trp Tyr Arg Pro Val Ala Gly Asp Phe Thr Pro Ala Ala Glu Ile Val
        35                  40                  45

Lys Asp Gly Asp Asp Ala Val Val Arg Leu Glu Leu Pro Gly Ile Asp
    50                  55                  60

Val Asp Lys Asn Val Glu Leu Asp Pro Gly Gln Pro Val Ser Arg Leu
65                  70                  75                  80

Val Ile Arg Gly Glu His Arg Asp Glu His Thr Gln Asp Ala Gly Asp
                85                  90                  95

Lys Asp Gly Arg Thr Leu Arg Glu Ile Arg Tyr Gly Ser Phe Arg Arg
            100                 105                 110

Ser Phe Arg Leu Pro Ala His Val Thr Ser Glu Ala Ile Ala Ala Ser
        115                 120                 125

Tyr Asp Ala Gly Val Leu Thr Val Arg Val Ala Gly Ala Tyr Lys Ala
    130                 135                 140

-continued

```
Pro Ala Glu Thr Gln Ala Gln Arg Ile Ala Ile Thr Lys
145                 150                 155

<210> SEQ ID NO 13
<211> LENGTH: 103
<212> TYPE: PRT
<213> ORGANISM: Mycobacterium tuberculosis

<400> SEQUENCE: 13

Cys Ile Arg Val Val Gly Gly Arg Ala Arg Met Ala Glu Pro Lys Leu
1               5                   10                  15

Gly Gln Pro Val Glu Trp Thr Pro Cys Arg Ser Ser Asn Pro Gln Val
            20                  25                  30

Lys Ile Pro Gly Gly Ala Leu Cys Gly Lys Leu Ala Val Pro Val Asp
        35                  40                  45

Tyr Asp Arg Pro Asp Gly Asp Val Ala Ala Leu Ala Leu Ile Arg Phe
    50                  55                  60

Pro Ala Thr Gly Asp Lys Ile Gly Ser Leu Val Ile Asn Pro Gly Gly
65                  70                  75                  80

Pro Gly Glu Ser Gly Ile Glu Ala Ala Leu Gly Val Phe Gln Thr Leu
                85                  90                  95

Pro Lys Arg Val His Glu Arg
            100

<210> SEQ ID NO 14
<211> LENGTH: 65
<212> TYPE: PRT
<213> ORGANISM: Mycobacterium tuberculosis

<400> SEQUENCE: 14

Thr Asn Ser Glu Ile Leu Ser Gly Ile Gly Ile Ser Leu Leu Ser Pro
1               5                   10                  15

Leu Ala Leu Ala Thr Asn Gly Ala Ala Ile Gly Ile Gly Leu Val Ala
            20                  25                  30

Gly Leu Ile Ala Pro Pro Leu Ala Val Ala Ala Asn Leu Ala Gly Ala
        35                  40                  45

Leu Pro Gly Ile Val Gly Gly Ala Pro Asn Pro Tyr Thr Tyr Pro Glu
    50                  55                  60

Asn
65

<210> SEQ ID NO 15
<211> LENGTH: 130
<212> TYPE: PRT
<213> ORGANISM: Mycobacterium tuberculosis

<400> SEQUENCE: 15

Asn Arg Leu Arg Ala Pro Leu Lys Val Thr Ser Asp Tyr Ser Pro Val
1               5                   10                  15

Phe Gly Cys Leu Phe Lys Gly Ile Ala Arg Gly Val Lys Glu Phe Ala
            20                  25                  30

Pro Leu Ile Gly Val Arg Lys Ala Gly Leu Phe Thr Ser Ser Ser Phe
        35                  40                  45

Val Leu Gly Ala Pro Ser Tyr Thr Tyr Pro Glu Ser Leu Pro Ile Val
    50                  55                  60

Asn Ala Ser Gly Gly Pro Asn Cys Arg Gly Leu Pro Asp Ile Pro Thr
65                  70                  75                  80

Lys Gln Thr Gly Gly Ser Phe Tyr Arg Ala Pro Phe Leu Val Thr Asp
```

-continued

```
                85                  90                  95
Asn Ala Leu Ile Pro Tyr Gln Pro Phe Thr Glu Leu Gln Val Asp Ala
            100                 105                 110

Pro Ser Thr Leu Gln Phe Leu Phe Asn Gly Ala Phe Ala Glu Arg Asp
        115                 120                 125

Asp Phe
    130

<210> SEQ ID NO 16
<211> LENGTH: 39
<212> TYPE: PRT
<213> ORGANISM: Mycobacterium tuberculosis

<400> SEQUENCE: 16

Trp Asp Ala Val Ala Gln Cys Glu Ser Gly Gly Asn Trp Ala Ala Asn
1               5                   10                  15

Thr Gly Asn Gly Lys Tyr Gly Gly Leu Gln Phe Lys Pro Ala Thr Trp
            20                  25                  30

Ala Ala Phe Gly Gly Val Gly
        35

<210> SEQ ID NO 17
<211> LENGTH: 66
<212> TYPE: PRT
<213> ORGANISM: Mycobacterium tuberculosis

<400> SEQUENCE: 17

Trp Asp Ala Val Ala Gln Cys Glu Ser Gly Gly Asn Trp Ala Ala Asn
1               5                   10                  15

Thr Gly Asn Gly Lys Tyr Gly Gly Leu Gln Phe Lys Pro Ala Thr Trp
            20                  25                  30

Ala Ala Phe Gly Gly Val Gly Asn Pro Ala Ala Ala Ser Arg Glu Gln
        35                  40                  45

Gln Ile Ala Val Ala Asn Arg Val Leu Ala Glu Gln Gly Leu Asp Ala
    50                  55                  60

Trp Pro
65

<210> SEQ ID NO 18
<211> LENGTH: 27
<212> TYPE: PRT
<213> ORGANISM: Mycobacterium tuberculosis

<400> SEQUENCE: 18

Ser Arg Thr Leu Tyr Leu Gly Gly Thr Thr Gly Pro Val Lys Phe Met
1               5                   10                  15

Asn Asp Val Gln Leu Ala Ala Leu Asp His Ala
            20                  25

<210> SEQ ID NO 19
<211> LENGTH: 98
<212> TYPE: PRT
<213> ORGANISM: Mycobacterium tuberculosis

<400> SEQUENCE: 19

Met Asp Pro Thr Leu Ser Tyr Asn Phe Gly Ile Glu His Ser Val
1               5                   10                  15

Arg Gln Glu Ile His Thr Thr Ser Ala Arg Phe Asn Ala Ala Leu Asp
            20                  25                  30

Glu Leu Arg Ala Arg Ile Ala Pro Leu Gln Gln Leu Trp Thr Ser Glu
```

```
                  35                  40                  45

Ala Ala Thr Ala Tyr Gln Ala Glu Gln Leu Lys Trp His Arg Ser Ala
 50                  55                  60

Thr Ala Leu Asn Glu Ile Leu Val Gln Leu Gly Asp Ala Val Arg Asp
 65                  70                  75                  80

Gly Ala Glu Glu Val Ala Asp Ala Asp Arg Arg Ala Ala Gly Val Trp
                 85                  90                  95

Ala Arg

<210> SEQ ID NO 20
<211> LENGTH: 45
<212> TYPE: PRT
<213> ORGANISM: Mycobacterium tuberculosis

<400> SEQUENCE: 20

Ala Val Ser Glu Pro Gly Gly His Ala His Ser Ala Gly Val Thr
 1               5                  10                  15

Val Ile Ala Gly Arg Pro Asp Ser Ser Gly Ala Arg Ala Ala Thr Leu
                 20                  25                  30

Pro Ser Arg Gln Ala Leu Leu Ala Asp Arg Asp Gly Thr
                 35                  40                  45

<210> SEQ ID NO 21
<211> LENGTH: 107
<212> TYPE: PRT
<213> ORGANISM: Mycobacterium tuberculosis

<400> SEQUENCE: 21

Ala Gln Ala Ala Ala Leu Gly Glu Ala Thr Gly Arg Gly Ala Gly Thr
 1               5                  10                  15

Val Ala Ala Asp Ala Thr Ala Pro Pro Ser Gly Ile Ile Ser Gln Leu
                 20                  25                  30

Leu Glu Ala Leu Gly Asn Ala Ser Arg Gly Tyr Met Asp Phe Trp Asp
                 35                  40                  45

Gln Val Leu Asn Thr Leu Thr Gly Ser Pro Leu Ala Gly Thr Thr Trp
 50                  55                  60

Gln Asn Thr Phe Gly Ile Leu Ala Asp Ile Gly Arg Phe Ser Thr Val
 65                  70                  75                  80

Ala Asn Asp Ser Met Ser Pro Ile Asn Leu Ala Met Thr Glu Phe Lys
                 85                  90                  95

Met Phe Tyr Lys Leu Pro Val Glu Gly Leu Asp
                 100                 105

<210> SEQ ID NO 22
<211> LENGTH: 170
<212> TYPE: PRT
<213> ORGANISM: Mycobacterium tuberculosis

<400> SEQUENCE: 22

Met Phe Ser Pro Ala Glu Met Ala Val Phe Ala Asp Arg Arg His Ile
 1               5                  10                  15

Ser Arg His Phe Arg Ile Gly Asn Ala Leu Ala Thr Arg Ala Glu Ile
                 20                  25                  30

Leu Asp Met Thr Asn Leu Cys Lys Leu Leu Val Lys Ser Val Val Val
                 35                  40                  45

Gly Gly Phe Val Ala Ala Ser Met Ala Ser Ser Thr Gly Val Val Ser
 50                  55                  60

Ala Glu Pro Thr Pro Asn Trp Asp Ala Ile Ala Gln Cys Glu Ser Gly
```

```
                65                  70                  75                  80
Gly Asn Trp His Ala Asn Thr Gly Asn Gly Glu Tyr Gly Gly Leu Gln
                85                  90                  95

Phe Lys Pro Ala Thr Trp Ala Arg Tyr Gly Gly Val Gly Asn Pro Ala
            100                 105                 110

Ala Ala Ser Arg Glu Gln Gln Ile Ala Val Ala Asn Arg Val Phe Ala
            115                 120                 125

Glu Glu Gly Val Glu Pro Trp Pro Lys Cys Gly Ala Gln Ser Gly Leu
            130                 135                 140

Pro Ile Gly Trp Tyr Ser His Pro Ala Gln Gly Ile Lys Gln Ile Ile
145                 150                 155                 160

Asn Gly Leu Ile Gln Ala Ala Val Pro Arg
                165                 170

<210> SEQ ID NO 23
<211> LENGTH: 184
<212> TYPE: PRT
<213> ORGANISM: Mycobacterium tuberculosis

<400> SEQUENCE: 23

Val Asp Leu Pro Gly Asn Asp Phe Asp Ser Asn Asp Phe Asp Ala Val
1               5                   10                  15

Asp Leu Trp Gly Ala Asp Gly Ala Glu Gly Trp Thr Ala Asp Pro Ile
            20                  25                  30

Ile Gly Val Gly Ser Ala Ala Thr Pro Asp Thr Gly Pro Asp Leu Asp
            35                  40                  45

Asn Ala His Gly Gln Ala Glu Thr Asp Thr Glu Gln Glu Ile Ala Leu
    50                  55                  60

Phe Thr Val Thr Asn Pro Pro Arg Thr Val Ser Val Ser Thr Leu Met
65                  70                  75                  80

Asp Gly Arg Ile Asp His Val Glu Leu Ser Ala Arg Val Ala Trp Met
                85                  90                  95

Ser Glu Ser Gln Leu Ala Ser Glu Ile Leu Val Ile Ala Asp Leu Ala
            100                 105                 110

Arg Gln Lys Ala Gln Ser Ala Gln Tyr Ala Phe Ile Leu Asp Arg Met
            115                 120                 125

Ser Gln Gln Val Asp Ala Asp Glu His Arg Val Ala Leu Leu Arg Lys
            130                 135                 140

Thr Val Gly Glu Thr Trp Gly Leu Pro Ser Pro Glu Glu Ala Ala Ala
145                 150                 155                 160

Ala Glu Ala Glu Val Phe Ala Thr Arg Tyr Ser Asp Cys Pro Ala
                165                 170                 175

Pro Asp Asp Glu Ser Asp Pro Trp
            180
```